US012629342B1

(12) United States Patent
Schindler et al.

(10) Patent No.: US 12,629,342 B1
(45) Date of Patent: May 19, 2026

(54) SYSTEMS, METHODS, AND APPARATUSES FOR DELIVERY OF ACTIVE COMPOUNDS

(71) Applicant: Textile-Based Delivery, Inc., Conover, NC (US)

(72) Inventors: Jordan Schindler, Charlotte, NC (US); Michael Drzewinski, Denver, NC (US)

(73) Assignee: Textile-Based Delivery, Inc., Conover, NC (US)

( * ) Notice: Subject to any disclaimer, the term of this patent is extended or adjusted under 35 U.S.C. 154(b) by 360 days.

(21) Appl. No.: 18/125,366

(22) Filed: Mar. 23, 2023

Related U.S. Application Data

(60) Provisional application No. 63/323,288, filed on Mar. 24, 2022.

(51) Int. Cl.
| | |
|---|---|
| *A61K 9/70* | (2006.01) |
| *D03D 15/283* | (2021.01) |
| *G16H 10/60* | (2018.01) |
| *G16H 40/67* | (2018.01) |

(52) U.S. Cl.
CPC ............. *A61K 9/70* (2013.01); *D03D 15/283* (2021.01); *G16H 10/60* (2018.01); *G16H 40/67* (2018.01); *D10B 2401/04* (2013.01); *D10B 2401/16* (2013.01); *D10B 2401/18* (2013.01); *D10B 2501/00* (2013.01)

(58) Field of Classification Search
None
See application file for complete search history.

(56) References Cited

U.S. PATENT DOCUMENTS

| | | | |
|---|---|---|---|
| 7,942,867 B2 | 5/2011 | Hood et al. | |
| 9,847,155 B2 | 12/2017 | Kim et al. | |
| 10,021,188 B2 * | 7/2018 | Oleson et al. | H04L 67/12 |
| | | | 709/201 |
| 10,145,622 B2 | 12/2018 | Leonard | |
| 10,153,065 B2 | 12/2018 | Tsukada et al. | |
| 10,279,200 B2 | 5/2019 | Hyde et al. | |
| 10,605,680 B2 | 3/2020 | Sun | |
| 11,129,554 B2 | 9/2021 | Heikenfeld | |
| 2017/0173262 A1 | 6/2017 | Veltz | |
| 2021/0095401 A1 * | 4/2021 | Bowles et al. | D04B 1/12 |

FOREIGN PATENT DOCUMENTS

| | | | | | |
|---|---|---|---|---|---|
| CN | 107847934 A | * | 3/2018 | | B01L 3/00 |
| WO | WO 2019222845 | * | 12/2019 | | A61B 5/7455 |

* cited by examiner

*Primary Examiner* — Ula C Ruddock
(74) *Attorney, Agent, or Firm* — Neo IP

(57) ABSTRACT

Drug delivery systems and wearable articles including the drug delivery systems are provided. The drug delivery systems include yarns, yarn precursors, threads, filaments, and/or fibers coated with at least one polymer and at least one active compound. The drug delivery systems include at least one conductive and/or electromagnetic yarn, yarn precursor, thread, filament, and/or fiber. The drug delivery systems further include biometric data, environmental data, and at least one remote device. Parameters of the wearable articles are operable to be adjusted based on the biometric data and/or the environmental data.

20 Claims, 4 Drawing Sheets

SYSTEMS, METHODS, AND APPARATUSES FOR DELIVERY OF ACTIVE COMPOUNDS

CROSS REFERENCES TO RELATED APPLICATIONS

This application claims priority to and the benefit of U.S. Provisional Patent Application No. 63/323,288, filed Mar. 24, 2022, which is incorporated herein by reference in its entirety.

BACKGROUND OF THE INVENTION

1. Field of the Invention

The present invention relates to smart textiles, and more specifically to systems, methods, and apparatuses for delivering active compounds.

2. Description of the Prior Art

It is generally known in the prior art to provide smart textiles. It also generally known in the prior art to provide drug delivery devices.

Prior art patent documents include the following:

U.S. Patent Publication No. 20210095401 for Composite textile structure for sensing, activation, and signal network by inventors Bowles, et al., filed Sep. 30, 2020 and published Apr. 1, 2021, is directed to structures for sensing, activation, and signal networking in a composite textile. The publication discloses that a composite textile can comprise an activation layer of a reactive yarn knit into a fabric. The reactive yarn can have at least one physical property that changes in response to a stimulus. A signaling layer of a first conductive yarn can be knit into the fabric with the activation layer. The first conductive yarn provides the stimulus to the reactive yarn. A sensing layer comprising second conductive yarn can be knit into the fabric with the activation layer and signaling layer. The second conductive yarn can provide a feedback signal corresponding to the stimulus provided by the first conductive yarn of the signaling layer.

U.S. Pat. No. 10,145,622 for Textile thread or fibre by inventor Leonard, filed Jun. 6, 2017 and issued Dec. 4, 2018, is directed to a textile fiber, thread or yarn. The fiber, thread or yarn is generally for production into a fabric. Alternative aspects are described for achieving a cooling effect, energy harvesting, heating, energy generation, energy emission, and others.

U.S. Patent Publication No. 20170173262 for Medical systems, devices and methods by inventor Veltz, filed Mar. 1, 2017 and published Jun. 22, 2017, is directed to a medical system comprising one or more sensors associated with one or more actuators. The publication describes sensors and/or actuators, logic circuits, user interfaces, association schemes, communication schemes, security schemes, cryptographic schemes, medical management rules, social mechanisms, energy management schemes, time and/or space schemes, body analytes and/or biomarkers, blood glucose and/or interstitial glucose sensors, drug delivery devices, continuous glucose monitoring devices, as well as flash glucose monitoring devices. Methods, software and other hardware aspects are described.

U.S. Pat. No. 9,847,155 for Method of manufacturing electrically conductive stretchable interconnect using twisted nature of yarn fibers by inventors Kim, et al., filed Jan. 26, 2016 and issued Dec. 19, 2017, is directed to an electrically conductive stretchable interconnect using a twisted nature of yarn fibers and a method of manufacturing the same. The patent discloses that the electrically conductive stretchable interconnect includes: an elastic body in which a stretchable tunnel is formed in a length direction; and a conductive twisted yarn including a stretchable structure positioned inside the stretchable tunnel and extended by a force applied in the length direction and an extending part extending from the stretchable structure to an outside of the elastic body.

U.S. Pat. No. 10,279,200 for Monitoring and treating pain with epidermal electronics by inventors Hyde, et al., filed Nov. 28, 2016 and issued May 7, 2019, is directed to systems and methods for monitoring, treating, and preventing a pain state of an individual. The patent discloses a system that includes, but is not limited to, a deformable substrate; a sensor assembly coupled to the deformable substrate, the sensor assembly including a motion sensor and a physiological sensor, the sensor assembly configured to generate one or more sense signals based on detection of a movement of the body portion by the motion sensor and a physiological parameter of the body portion by the physiological sensor; a processor including circuitry configured to identify a physiological state of the individual subject based on at least one of the movement of the body portion or the physiological parameter; and an effector operably coupled to the processor and configured to affect the body portion responsive to control by the processor.

U.S. Pat. No. 11,129,554 for Sweat monitoring and control of drug delivery by inventor Heikenfeld, filed May 28, 2015 and issued Sep. 28, 2021, is directed to concentration of an administered compound, such as a drug, in an organ or a bodily fluid, such as blood, is determined directly through detecting the drug or its metabolites in sweat. The concentration may be determined indirectly by administering the drug together with one or more tracer compounds or metabolites thereof or by detecting concentrations and trends of other analytes present in the body that react to the presence of the drug. By determining tracer concentration in sweat, the concentration of the drug in blood or an organ can be determined. The tracer is a compound selected for ease of detection in sweat, known metabolic and solubility profiles that correspond to those of the drug, and safety of use. A smart transdermal delivery patch is used to administer a dosage of drug to a wearer in coordination with at least one sweat sensor reading conveying information about the wearer.

U.S. Pat. No. 10,153,065 for Conductive polymer fibers, method and device for producing conductive polymer fibers, biological electrode, device for measuring biological signals, implantable electrode, and device for measuring biological signals by inventors Tsukada, filed Nov. 16, 2012 and issued Dec. 11, 2018, is directed to conductive polymer fibers, in which a conductor containing a conductive polymer impregnates and/or adheres to base fibers, and the aforementioned conductive polymer is PEDOT-PSS.

U.S. Pat. No. 10,605,680 for Devices for static and dynamic body measurements by inventor Sun, filed Sep. 17, 2019 and issued Mar. 31, 2020, is directed to measuring static and dynamic forces of a body using sensors. In particular, a sensor may include a first layer serving as a flexible support material; a second layer on the first layer, the second layer serving as a sensing material; and a third layer on the second layer, the third layer comprising an insulating material. Further, the second layer and the third layer may be coupled using a first electrode comprising a first conductive thread and a first non-conductive thread, and the first conductive thread may be embedded in the second layer. Also, the first layer and the second layer may be further coupled using a second electrode comprising a second conductive thread and a second non-conductive thread, and the second conductive thread may be embedded in the second layer. The patent discloses that the sensor is stitched, threaded, embroidered, sewn, adhered, and so on, into apparel, such as socks, gloves, shirts, pants, undergarments, hats, and so on.

U.S. Pat. No. 7,942,867 for Remotely controlled substance delivery device, filed Jan. 18, 2006 and issued May 17, 2011, is directed to a system including a remotely controlled substance delivery device and associated controller. Methods of use and control of the device are also disclosed. The patent discloses that a delivery device or related device may be placed in an environment in order to pump a material into the environment or into an additional fluid handling structure within the device. Exemplary environments include a body of an organism, a body of water, or an enclosed volume of a fluid. The concentration of a substance in the fluid to be delivered may be modified by a remote control signal. The patent discloses that a magnetic field, an electric field, or electromagnetic control signal may be used.

SUMMARY OF THE INVENTION

The present invention relates to smart textiles, and more specifically to systems, methods, and apparatuses for delivering active compounds.

It is an object of this invention to provide delivery of active compounds via a wearable article or garment. In one embodiment, the wearable article or garment includes at least one conductive and/or electromagnetic yarn, yarn precursor, thread, filament, and/or fiber.

In one embodiment, the present invention provides an article for delivery of an active compound to the skin of a user including a textile including at least one printed circuit board (PCB), wherein the at least one PCB includes a processor, a heater, a memory, and a battery, wherein the textile includes at least one electromagnetic fiber and at least one loaded fiber, wherein the loaded fiber includes a polymeric matrix including at least one active compound, wherein a heater is operable to generate a voltage, wherein the voltage is conducted by the at least one electromagnetic fiber, wherein increasing the voltage increases the temperature of the loaded fiber, wherein increasing the temperature of the loaded fiber increases the rate of release of the at least one active compound, and wherein decreasing the voltage decreases the temperature of the loaded fiber, wherein decreasing the temperature of the loaded fiber decreases the rate of release of the at least one active compound.

In another embodiment, the present invention provides system for automatic delivery of an active compound to the skin of a user including a textile, at least one user device, and at least one server including at least one database, wherein the at least one server is in network communication with the at least one user device, wherein the at least one database stores at least one user profile and at least one set of parameters for data correlating to the at least one user profile associated with the at least one user device, wherein the textile includes a printed circuit board (PCB) and at least one sensor, wherein the at least one sensor collects physiological data and/or environmental data relating to a physiological condition and/or an environmental condition associated with the at least one user profile, wherein the at least one sensor is operable to transmit the physiological data and/or the environmental data to the at least one user device, wherein the at least one user device is operable to determine that the physiological data and/or the environmental data does not meet the at least one set of parameters, wherein the textile further comprises at least one electromagnetic fiber and at least one loaded fiber, wherein the at least one loaded fiber comprises a polymeric matrix including an active compound, wherein a processor of the at least one PCB receives a signal from the at least one user device, wherein a heater generates a voltage in response to the received signal, wherein the voltage is conducted by the at least one electromagnetic fiber, wherein increasing the voltage increases the temperature of the loaded fiber, wherein increasing the temperature of the loaded fiber increases the rate of release of the at least one active compound, and wherein decreasing the voltage decreases the temperature of the loaded fiber, wherein decreasing the temperature of the loaded fiber decreases the rate of release of the at least one active compound.

In yet another embodiment, the present invention provides system for automatic delivery of an active compound to the skin of a user including a textile including at least one printed circuit board (PCB) and a heater, wherein the at least one PCB includes a processor, a memory, and a battery, and at least one user device and at least one server including at least one database, wherein the at least one server is in network communication with the at least one user device, wherein the at least one user device is in network communication with the at least one PCB, wherein the textile includes at least one electromagnetic fiber and at least one loaded fiber, wherein the at least one loaded fiber includes an active compound dispersed within a polymeric matrix, wherein the at least one PCB receives a signal from the at least one user device to trigger the release of the active compound from the at least one loaded fiber, and wherein the at least one PCB transmits the signal to the heater, wherein the heater applies a voltage to the at least one electromagnetic fiber.

These and other aspects of the present invention will become apparent to those skilled in the art after a reading of the following description of the preferred embodiment when considered with the drawings, as they support the claimed invention.

DETAILED DESCRIPTION

Figure 1:
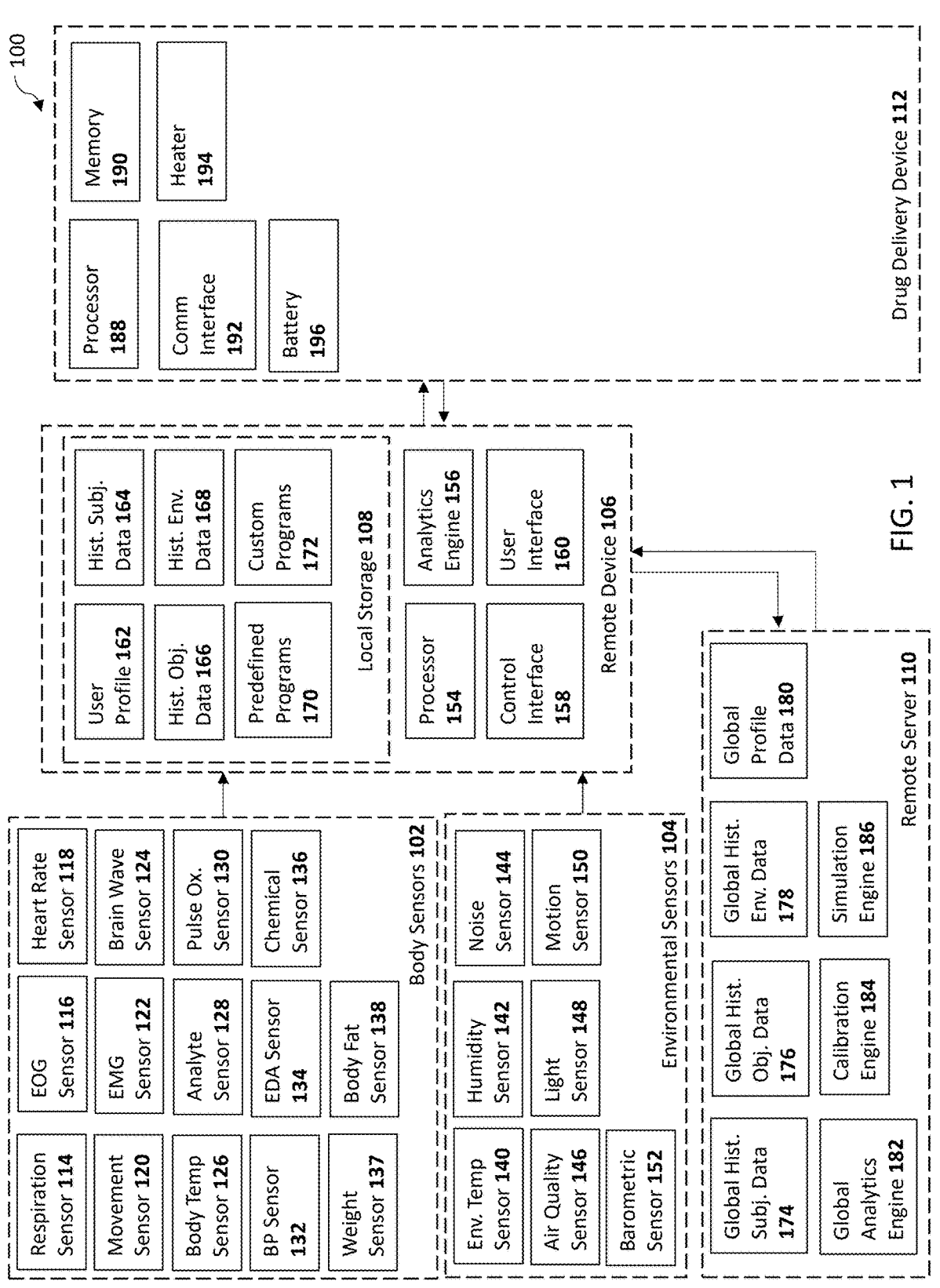
FIG. 1 is a block diagram of one embodiment of the delivery system.

The present invention is generally directed to smart textiles, and more specifically to systems, methods, and apparatuses for delivering active compounds.

In one embodiment, the present invention provides an article for delivery of an active compound to the skin of a user including a textile including at least one printed circuit board (PCB), wherein the at least one PCB includes a processor, a heater, a memory, and a battery, wherein the textile includes at least one electromagnetic fiber and at least one loaded fiber, wherein the loaded fiber includes a polymeric matrix including at least one active compound, wherein a heater is operable to generate a voltage, wherein the voltage is conducted by the at least one electromagnetic fiber, wherein increasing the voltage increases the temperature of the loaded fiber, wherein increasing the temperature of the loaded fiber increases the rate of release of the at least one active compound, and wherein decreasing the voltage decreases the temperature of the loaded fiber, wherein decreasing the temperature of the loaded fiber decreases the rate of release of the at least one active compound.

In another embodiment, the present invention provides a system for automatic delivery of an active compound to the skin of a user including a textile, at least one user device, and at least one server including at least one database, wherein the at least one server is in network communication with the at least one user device, wherein the at least one database stores at least one user profile and at least one set of parameters for data correlating to the at least one user profile associated with the at least one user device, wherein the textile includes a printed circuit board (PCB) and at least one sensor, wherein the at least one sensor collects physiological data and/or environmental data relating to a physiological condition and/or an environmental condition associated with the at least one user profile, wherein the at least one sensor is operable to transmit the physiological data and/or the environmental data to the at least one user device, wherein the at least one user device is operable to determine that the physiological data and/or the environmental data does not meet the at least one set of parameters, wherein the textile further comprises at least one electromagnetic fiber and at least one loaded fiber, wherein the at least one loaded fiber comprises a polymeric matrix including an active compound, wherein a processor of the at least one PCB receives a signal from the at least one user device, wherein a heater generates a voltage in response to the received signal, wherein the voltage is conducted by the at least one electromagnetic fiber, wherein increasing the voltage increases the temperature of the loaded fiber, wherein increasing the temperature of the loaded fiber increases the rate of release of the at least one active compound, and wherein decreasing the voltage decreases the temperature of the loaded fiber, wherein decreasing the temperature of the loaded fiber decreases the rate of release of the at least one active compound.

In yet another embodiment, the present invention provides a system for automatic delivery of an active compound to the skin of a user including a textile including at least one printed circuit board (PCB) and a heater, wherein the at least one PCB includes a processor, a memory, and a battery, and at least one user device and at least one server including at least one database, wherein the at least one server is in network communication with the at least one user device, wherein the at least one user device is in network communication with the at least one PCB, wherein the textile includes at least one electromagnetic fiber and at least one loaded fiber, wherein the at least one loaded fiber includes an active compound dispersed within a polymeric matrix, wherein the at least one PCB receives a signal from the at least one user device to trigger the release of the active compound from the at least one loaded fiber, and wherein the at least one PCB transmits the signal to the heater, wherein the heater applies a voltage to the at least one electromagnetic fiber.

It is generally known in the prior art to provide drug delivery systems. See, e.g., Staples M, Daniel K, Cima M J, Langer R. Application of micro- and nano-electromechanical devices to drug delivery. Pharm Res. 2006 May 23 (5): 847-63. doi: 10.1007/s11095-006-9906-4. Epub 2006 May 5. PMID: 16715375, which is incorporated herein by reference in its entirety. However, these systems often require an implanted device (e.g., artificial pancreas). There is a long standing, unmet need for drug delivery systems that are non-invasive and easy to maintain (e.g., machine washable). Further, there is a long standing, unmet need for textile-based delivery systems that include at least one conductive and/or electromagnetic yarn, yarn precursor, thread, filament, and/or fiber. The textile-based delivery systems of the present invention are operable to vary delivery of at least one active compound based on input (e.g., manual input, input from a remote device). Additionally, the textile-based delivery systems of the present invention are operable to include a feedback loop to vary delivery of at least one active compound based on body sensor data, environmental data, and/or location data.

None of the prior art discloses a system for delivering active compounds using at least one conductive and/or electromagnetic yarn, yarn precursor, thread, filament, and/or fiber. Further, none of the prior art discloses a system for delivering active compounds using at least one conductive and/or electromagnetic yarn, yarn precursor, thread, filament, and/or fiber based on biometric and/or environmental data.

Referring now to the drawings in general, the illustrations are for the purpose of describing one or more preferred embodiments of the invention and are not intended to limit the invention thereto.

FIG. 1 is a block diagram of one embodiment of a delivery system. The delivery system 100 includes body sensors 102, environmental sensors 104, a remote device 106 with local storage 108, a remote server 110, and at least one delivery device 112. In a preferred embodiment, the body sensors 102 and/or the environmental sensors 104 are operable to measure biometric data and environmental data, respectively, in real time and/or near-real time.

The body sensors 102 include, but are not limited to, a respiration sensor 114, an electrooculography (EOG) sensor 116, a heart rate sensor 118, a movement sensor 120, an electromyography (EMG) sensor 122, a brain wave sensor 124, a body temperature sensor 126, an analyte sensor 128, a pulse oximeter sensor 130, a blood pressure (BP) sensor 132, an electrodermal activity (EDA) sensor 134, an odor sensor 136, a body weight sensor 137, and/or a body fat sensor 138. In one embodiment, one or more of the body sensors 102 are incorporated into a wearable device (e.g., smart watch, ring, smart glasses, contact lenses). In another embodiment, one or more of the body sensors 102 is incorporated into the at least one delivery device 112. In yet another embodiment, one or more of the body sensors 102 is implanted. See, e.g., U.S. Pat. Nos. 7,125,382; 7,469,076; and 7,504,364, each of which is incorporated herein by reference in its entirety.

In one embodiment, the body sensors 102 include a piezoresistive, a piezocapactive, a piezoelectric, a piezophotronic, and/or a triboelectric sensor. See, e.g., Mirvakili, S. M., Langer, R. Wireless on-demand drug delivery. Nat Electron 4, 464-477 (2021). https://doi.org/10.1038/s41928-021-00614.9, which is incorporated herein by reference in its entirety. In one embodiment, the body sensors 102 include at least one graphene-based sensor. See, e.g., Huang H, Su S, Wu N, Wan H, Wan S, Bi H, Sun L. Graphene-Based Sensors for Human Health Monitoring. Front Chem. 2019 Jun. 11; 7:399. doi: 10.3389/fchem.2019.00399. PMID: 31245352; PMCID: PMC6580932, which is incorporated herein by reference in its entirety.

The respiration sensor 114 measures a respiratory rate. In one embodiment, the respiration sensor 114 is incorporated into a wearable device (e.g., ring, smart watch, a chest strap). In another embodiment, the respiration sensor 114 is incorporated into a patch or a bandage. In one embodiment, the respiratory rate is estimated from an electrocardiogram, a photoplethysmogram (e.g., a pulse oximeter), and/or an accelerometer. In yet another embodiment, the respiratory sensor 114 uses a non-contact motion biomotion sensor to monitor respiration.

The electrooculography (EOG) sensor 116 measures the cornea-retinal standing potential that exists between the front and the back of the eye. Measurements of eye movements are done by placing pairs of electrodes either above and below the eye or to the left and right of the eye. If the eye moves to a position away from the center and toward one of the electrodes, a potential difference occurs between the electrodes. The recorded potential is a measure of the eye's position. In one embodiment, the EOG sensor is incorporated into a wearable device (e.g., smart glasses).

The heart rate sensor 118 is preferably incorporated into a wearable device (e.g., APPLE WATCH®, SAMSUNG GALAXY®, FITBIT®, OURAR). Alternatively, the heart rate sensor 118 is attached to the user with a chest strap. In another embodiment, the heart rate sensor 118 is incorporated into a patch or a bandage. The heart rate is determined using electrocardiogramae oximetry, ballistocardiography, or seismocardiography. In one embodiment, the heart rate sensor 118 measures heart rate variability (HRV). HRV is a measurement of the variation in time intervals between heartbeats. A high HRV measurement is indicative of less stress, while a low HRV measurement is indicative of more stress. Studies have linked abnormalities in HRV to diseases where stress is a factor (e.g., diabetes, depression, congestive heart failure). In one embodiment, a Poincaré plot is generated to display HRV on a device such as a smartphone.

The movement sensor 120 is an accelerometer and/or a gyroscope. In one embodiment, the accelerometer and/or the gyroscope are incorporated into a wearable device (e.g., APPLE WATCH®, SAMSUNG GALAXY®, FITBIT®, OURAR, actigraph). In another embodiment, the accelerometer and/or the gyroscope are incorporated into a smartphone. In alternative embodiment, the movement sensor 120 is a non-contact sensor. In one embodiment, the movement sensor 120 is at least one piezoelectric sensor. In another embodiment, the movement sensor 120 is a pyroelectric infrared sensor (i.e., a "passive" infrared sensor). Alternatively, the movement sensor 120 is incorporated into a smart fabric.

The electromyography (EMG) sensor 122 records the electrical activity produced by skeletal muscles. Impulses are recorded by attaching electrodes to the skin surface over the muscle. In one embodiment, two electrodes are placed on the inside of each calf muscle about 2 to 4 cm (about 0.8 to 1.6 inches) apart. In yet another embodiment, two electrodes are placed over the anterior tibialis of each leg. The electrodes on the leg are operable to be used to detect movement of the legs during sleep, which may occur with Restless Leg Syndrome or Periodic Limb Movements of Sleep.

The brain wave sensor 124 is preferably an electroencephalogram (EEG) with at least one channel. In a preferred embodiment, the EEG has at least two channels. Multiple channels provide higher resolution data. The frequencies in EEG data indicate particular brain states. The brain wave sensor 124 is preferably operable to detect delta, theta, alpha, beta, and gamma frequencies. In another embodiment, the brain wave sensor 124 is operable to identify cognitive and emotion metrics, including focus, stress, excitement, relaxation, interest, and/or engagement. In yet another embodiment, the brain wave sensor 124 is operable to identify cognitive states that reflect the overall level of engagement, attention and focus and/or workload that reflects cognitive processes (e.g., working memory, problem solving, analytical reasoning).

The body temperature sensor 126 measures core body temperature and/or skin temperature. The body temperature sensor 126 is a thermistor, an infrared sensor, or thermal flux sensor. In one embodiment, the body temperature sensor 126 is incorporated into a wearable device (e.g., ring, smart watch). In another embodiment, the body temperature sensor 126 is incorporated into a patch or a bandage. The body temperature sensor 126 is preferably wireless.

The analyte sensor 128 monitors levels of an analyte in blood, sweat, or interstitial fluid. In one embodiment, the analyte is an electrolyte, a small molecule (molecular weight <900 Daltons), a protein (e.g., C-reactive protein), a biomarker, and/or a metabolite. In another embodiment, the analyte is glucose, lactate, glutamate, oxygen, sodium, chloride, potassium, calcium, ammonium, copper, magnesium, iron, zinc, creatinine, uric acid, oxalic acid, urea, ethanol, an amino acid, a hormone (e.g., cortisol, melatonin), a steroid, a neurotransmitter, a catecholamine, a cytokine, and/or an interleukin (e.g., IL-6). In one embodiment, the analyte sensor 128 is a blood sugar sensor. In one embodiment, the analyte sensor 128 monitors a sleep cycle (e.g., melatonin). The analyte sensor 128 is preferably non-invasive. Alternatively, the analyte sensor 128 is minimally invasive or implanted. In one embodiment, the analyte sensor 128 is incorporated into a wearable device (e.g., contact lenses). Alternatively, the analyte sensor 128 is incorporated into a patch or a bandage.

The pulse oximeter sensor 130 monitors oxygen saturation. In one embodiment, the pulse oximeter sensor 130 is worn on a finger, a toe, or an ear. In another embodiment, the pulse oximeter sensor 130 is incorporated into a patch or a bandage. The pulse oximeter sensor 130 is preferably wireless.

In one embodiment, the blood pressure (BP) sensor 132 is a sphygmomanometer. The sphygmomanometer is preferably wireless. In another embodiment, the blood pressure sensor 132 estimates the blood pressure without an inflatable cuff. In one embodiment, the blood pressure sensor 132 is incorporated into a wearable device (e.g., ring, smart watch).

The electrodermal activity (EDA) sensor 134 measures sympathetic nervous system activity. Electrodermal activity is more likely to have high frequency peak patterns (i.e., "storms") during deep sleep. In one embodiment, the electrodermal activity sensor 134 is incorporated into a wearable device (e.g., smart watch, ring). Alternatively, the electrodermal activity sensor 134 is incorporated into a patch or a bandage.

The chemical sensor 136 is preferably operable to detect at least one chemical including, but not limited to, gas vapor and/or body odor. Examples of chemical sensors include those disclosed in WIPO Publication No. 2018230382, U.S. Pat. Nos. 7,998,416 and 8,950,238, and U.S. Publication Nos. 20200096476 and 20200132631, each of which is incorporated herein by reference in its entirety.

The body weight sensor 137 is preferably a smart scale (e.g., FITBIT® ARIA®).

The body fat sensor 138 is preferably a bioelectrical impedance device. In one embodiment, the body fat sensor 138 is incorporated into a smart scale (e.g., FITBIT® ARIA®). Alternatively, the body fat sensor 138 is a handheld device.

In one embodiment, one or more of the body sensors 102 is incorporated in a flexible and wearable sensor. Examples of flexible and wearable sensors are disclosed in Ha M, Lim S, Ko H. Wearable and flexible sensors for user-interactive health-monitoring devices. J Mater Chem B. 2018 Jun. 28; 6(24): 4043-4064. doi: 10.1039/c8tb01063c. Epub 2018 Jun. 6. PMID: 32255149, which is incorporated herein by reference in its entirety.

The environmental sensors 104 include an environmental temperature sensor 140, a humidity sensor 142, a noise sensor 144, an air quality sensor 146, a light sensor 148, a motion sensor 150, and/or a barometric sensor 152. In one embodiment, the environmental temperature sensor 140, the humidity sensor 142, the noise sensor 144, the air quality sensor 146, the light sensor 148, the motion sensor 150, and/or the barometric sensor 152 are incorporated into a home automation system (e.g., NEST®). Alternatively, the environmental temperature sensor 140, the humidity sensor 142, the noise sensor 144, and/or the light sensor 148 are incorporated into the remote device 106 (e.g., smartphone, tablet). In one embodiment, the noise sensor 144 is a microphone. In one embodiment, the air quality sensor 146 measures carbon monoxide, carbon dioxide, nitrogen dioxide, sulfur dioxide, particulates, and/or volatile organic compounds (VOCs). In another embodiment, environmental data is obtained from third party sources (e.g., weather application).

The remote device 106 is preferably a smartphone or a tablet. Alternatively, the remote device 106 is a laptop or a desktop computer. The remote device 106 includes a processor 154, an analytics engine 156, a control interface 158, and a user interface 160. The remote device 106 accepts data input from the body sensors 102 and/or the environmental sensors 104. The remote device also accepts data input from the remote server 110. The remote device 106 stores data in a local storage 108. In one embodiment, the remote device 106 further includes at least one location sensor (e.g., Global Positioning System (GPS) sensor) and/or a camera operable to capture an image (e.g., still, video).

The local storage 108 on the remote device 106 includes a user profile 162, historical subjective data 164, historical objective data 166, historical environmental data 168, predefined programs 170, and/or custom programs 172. The user profile 162 stores system preferences and information about the user, including but not limited to, age, weight, height, gender, medical history (e.g., medications, diseases), fitness (e.g., fitness level, fitness activities), health goals, stress level, and/or lifestyle information. The medical history includes, but is not limited to, medication information, nutrition information (e.g., caffeine consumption, alcohol consumption), blood pressure, restless leg syndrome, headaches, heart disease, diabetes, insomnia, anxiety, neurological disorders, childhood illnesses, major adult illnesses, past surgical history (e.g., type, date, location), medications (e.g., prescription, over the counter), supplements (e.g., vitamins), allergies, prior injuries (e.g., motor vehicle accidents, falls), prior hospitalizations, prior transfusions, and/or immunizations.

In one embodiment, the medical history is stored in an implanted chip. See, e.g., U.S. Pat. Nos. 7,981,025; 8,747,313; 9,700,292; 9,974,492; 10,424,837; and/or 11,189,368, each of which is incorporated herein by reference in its entirety. In one embodiment, the implanted chip is readable using the remote device 106. In one embodiment, the implanted chip includes a radio frequency identification (RFID) transponder. In one embodiment, the RFID transponder is a passive RFID transponder.

In one embodiment, the weight and/or body fat percentage of the user is automatically uploaded to the local storage from a third-party application. In one embodiment, the third-party application obtains the information from a smart scale (e.g., FITBIT® ARIA®).

The historical objective data 166 includes information gathered from the body sensors 102. This includes information from the respiration sensor 114, the electrooculography (EOG) sensor 116, the heart rate sensor 118, the movement sensor 120, the electromyography (EMG) sensor 122, the brain wave sensor 124, the body temperature sensor 126, the analyte sensor 128, the pulse oximeter sensor 130, the blood pressure (BP) sensor 132, the electrodermal activity (EDA) sensor 134, the odor sensor 136, the body weight sensor 137, and/or the body fat sensor 138.

The historical environmental data 168 includes information gathered from the environmental sensors 104. This includes information from the environmental temperature sensor 140, the humidity sensor 142, the noise sensor 144, the air quality sensor 146, the light sensor 148, the motion sensor 150, and/or the barometric sensor 152. The historical subjective data 164 includes information regarding subjective observations of a user. The predefined programs 170 are general settings for various conditions and/or delivery devices. The custom programs 172 are settings (e.g., delivery device, various conditions) defined via user input. The custom programs 172 allow saving preferred settings (e.g., via user input).

The remote server 110 includes global historical subjective data 174, global historical objective data 176, global historical environmental data 178, global profile data 180, a global analytics engine 182, a calibration engine 184, and a simulation engine 186. The global historical subjective data 174, the global historical objective data 176, the global historical environmental data 178, and the global profile data 180 include data from multiple users. The calibration engine 184 is operable to calibrate the at least one delivery device. The simulation engine 186 is operable to determine optimal parameters for the at least one delivery device based on information from the body sensors 102, the environmental sensors 104, the remote device 106, the global historical subjective data 174, the global historical objective data 176, the global historical environmental data 178, and/or the global profile data 180.

The system further includes at least one delivery device 112. The at least one delivery device 112 is operable to deliver at least one active compound transdermally to skin of a user. In one embodiment, the at least one delivery device 112 includes at least one processor 188, at least one memory 190, a communications interface 192, a heater 194, and/or at least one battery 196. In one embodiment, one or more of the at least one body sensor 102 is incorporated into the at least one delivery device 112. In one embodiment, the heater 194 is operable to apply a direct current (DC) voltage to at least one conductive and/or electromagnetic yarn, yarn precursor, thread, filament, and/or fiber incorporated into the at least one delivery device 112. In one embodiment, the at least one delivery device 112 further includes a clock, a location sensor (e.g., Global Positioning System (GPS) sensor), and/or a pressure sensor. In one embodiment, the pressure sensor is operable to measure data related to swelling (e.g., reduction of swelling, increase in swelling). In another embodiment, the pressure sensor is operable to detect external force applied to the at least one delivery device. In one embodiment, the at least one delivery device 112 is operable to provide transcutaneous electrical nerve stimulation (TENS). See, e.g., U.S. Pat. Nos. 10,814,130; 9,572,708; 10,462,898; and 11,229,787 and U.S. Patent Publication Nos. 20170143977, 20200237031, 20200214624, and 20200188673, each of which is incorporated herein by reference in its entirety. In another embodiment, the at least one delivery device 112 is operable to provide haptic feedback and/or vibration.

By way of example, and not limitation, the at least one processor 188 is a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that is operable to perform calculations, process instructions for execution, and/or other manipulations of information. The communications interface 192 preferably includes a wireless communication interface for connecting to a network (not shown) and by which information is exchanged with other devices (e.g., remote device) connected to the network. Examples of wireless communication interfaces include, but are not limited to, an Intranet connection, Internet, ISM, BLUETOOTH® technology, WI-FI®, ZIGBEE®, WI-MAX, IEEE 802.11 technology, radio frequency (RF), Infrared Data Association (IrDA) compatible protocols, Local Area Networks (LAN), Wide Area Networks (WAN), Shared Wireless Access Protocol (SWAP), any combinations thereof, and other types of wireless networking protocols.

The body sensors 102, the environmental sensors 104, the remote device 106 with local storage 108, the remote server 110, and the at least one delivery device 112 are designed to connect wirelessly (e.g., BLUETOOTH®, WI-FI®, ZIGBEE®) through systems designed to exchange data between various data collection sources. In a preferred embodiment, the body sensors 102, the environmental sensors 104, the remote device 106 with local storage 108, the remote server 110, and the at least one delivery device 112 communicate wirelessly through BLUETOOTH®. Advantageously, BLUETOOTH® emits lower electromagnetic fields (EMFs) than WI-FI® and cellular signals.

The at least one delivery device is formed using yarns, yarn precursors, threads, fibers, filaments, textiles, and/or other substrates that are loaded with biologically active compounds, compositions, or ingredients (also referred to herein as "actives" and/or "active particles") that are integrated into the yarns, yarn precursors, threads, fibers, filaments, textiles, and/or substrates (e.g., films, sheets, cut and sew pieces, patches). These delivery systems are operable to be utilized to release the active compounds onto or into mammalian tissue, including, for example, human skin.

As used herein, the terms "yarn" and "yarn precursor" include not only finished yarns, but also starting or intermediate fiber-based materials from, e.g., greige cotton or extruded filament, to finished—and as described in certain embodiments, functionalized—yarns (e.g., yarns that are loaded with an active compound), whether on, e.g., a cone or spool or in a textile or fabric. The term "yarn" is also operable to be used to describe individual threads and spun and/or twisted threads. In some embodiments, the yarn is bulked or textured. Bulked and/or textured yarns are operable to refer to yarns that have been treated mechanically, chemically, or physically (e.g., tension-adjusted) so as to appear to have greater or increased volume relative to the yarn prior to mechanical, chemical, or physical treatment. For example, bulked and/or textured yarns are operable to have a crimped, coiled, or spiral configuration rather than a linear or stretched configuration. Bulked and/or textured yarns are operable to exhibit favorable properties over, e.g., partially-oriented yarn (POY) or other yarns lacking texture and/or bulk.

A number of advantages accompany the maintenance of bulk or texture in yarns loaded with active compounds as disclosed herein including, but not limited to, comfort, compatibility with established textile production, and/or high surface area in the non-occluded segments of the yarn. One factor to maintaining texture is selecting the coating and the matrix polymer such that they rapidly skin-over upon application. In some embodiments, this is achieved by applying solvent-free (e.g., water-free) matrix polymers and coatings, as aqueous dispersions (often denoted "latex" coatings or paints) may not readily yield a textured or bulked final yarn upon application to a textured or bulked precursor, unless strong conditions are used to flash off the water in a very short time (e.g., one second or less).

Embodiments of this disclosure provide yarns, yarn precursors, threads, filaments, fibers, fabrics, and other textiles, and other substrates that release therapeutically effective amounts of active compounds (e.g., organic active compounds) to the skin of a mammal. Such active compounds are operable to be selected for their dermatological and/or cosmetic benefit, e.g., for skin health and beauty. The active compounds are operable to penetrate into the skin or be delivered to tissue below the skin, including to the bloodstream. In certain embodiments, the active compound(s) are operable to penetrate into or through the skin to a depth that depends on the active concentration, the yarn-to-skin (or substrate-to-skin) contact time, physicochemical properties of the active, and/or the structure and condition of the skin.

Embodiments of this disclosure also provide yarns, yarn precursors, threads, filaments, fibers, textiles, and/or other substrates that release a therapeutically effective amount of active compound into the bloodstream of a mammal from outside the body. For instance, in one embodiment, this includes transdermal delivery, wherein contact of the yarn, the yarn precursor, the thread, the filament, the fiber, the textile, or the substrate with mammalian skin results in transfer of one or more active compounds through the skin and into the bloodstream. Textiles, fabrics, clothing, or apparel including yarns, yarn precursors, threads, filaments, fibers, and/or other substrates that deliver or release therapeutic amounts of active compounds to, or through, the skin of a mammal that makes contact with the textile, the fabric, the clothing, or the apparel are also provided.

Embodiments of this disclosure also provide yarns, yarn precursors, threads, filaments, fibers, textiles, fabrics, and/or substrates that are able to withstand washing and other stresses (e.g., physical, chemical, thermal, weather) with minimal or no loss of active. Thus, the present invention provides cold washable and hot-washable yarns, yarn precursors, threads, filaments, fibers, textiles, fabrics, and/or substrates that are loaded with active. For example, in a normal washing machine hot wash cycle, these yarns, yarn precursors, threads, filaments, fibers, textiles, fabrics, and/or substrates are operable to lose less than about 25%, less than about 12%, less than about 7%, less than about 3%, or less than about 1% of the active that was present in the material just before the wash.

The embodiments of the present disclosure include individual yarns, yarn precursors, threads, filaments, fibers, and other substrates, which are operable to provide flexibility through the blending of various active-loaded yarns, yarn precursors, threads, filaments, fibers, and other substrates. Advantageously, the embodiments of the present disclosure further provide low shipping costs to overseas mills and markets, especially as compared to finished fabrics (because the medicated yarn need only be a small fraction of the overall fabric yarn). Furthermore, the present invention provides the ability to provide the consumer with medicated thread that is operable to be applied to a fabric with a household sewing machine. The present invention further provides the opportunity to produce a product that is earlier—farther upstream—in the value-added chain that spans from raw fiber to finished textile.

Furthermore, the various embodiments of the present disclosure are operable to include or utilize cross-linked, hydrophobic polymers (e.g., elastomers such as silicone, rubbers and fluoroelastomers) as protective matrices for actives. Cross-linking (also referred to as "curing," "vulcanizing," and "thermosetting") applied to a dispersion or suspension of active particles in a polymer, oligomer, or monomer matrix—such as a Room Temperature Vulcanizer (RTV), commercial coating or adhesive, chemically reactive linear polymer, etc.—is operable to be employed by the various embodiments of the present disclosure for preparing yarns, yarn precursors, threads, filaments, fibers, textiles, fabrics, or substrates to protect the active against excessive loss during laundering, as well as against a wide range of chemical degradation reactions including hydrolysis, oxidation (depending on the polymer), acid/base-catalyzed reactions, etc. The polymer matrices are operable to be formed from various polymer- or oligomer-based systems, including commercially available elastomeric adhesives, glues, coatings, caulks, sealants, casting materials, and cross-linking systems. The polymers (e.g., elastomers) are also operable to be formed from one or more monomers.

In specific embodiments, the polymers (e.g., elastomers) are used as a vehicle to load one or more actives into and/or onto the yarn, yarn precursor, thread, filament, fiber, textile, or other substrate and/or immobilize the one or more actives in and/or on the yarn, yarn precursor, thread, filament, fiber, textile, or other substrate. For example, in particular embodiments, one or more actives is combined with a polymer (e.g., elastomer) to form a mixture or solution, which is applied to a yarn, yarn precursor, thread, filament, fiber, textile, or other substrate. In some embodiments, the final cross-linking (or all of the cross-linking, in some cases including polymerization) occurs in the presence of the dispersed or suspended active particles-resulting in a configuration in which local stresses and strains on the polymer associated with "forcing" solid active particles into an already-cross-linked polymer (e.g., elastomer) are minimized or eliminated. Such strains, at least at high active loadings, are operable to lead to higher permeability and loss of active-protecting effect. Entry of solid active particles (e.g., crystals) into, or formation inside, a previously cross-linked polymeric (e.g., elastomeric) core are also operable to cause distortion of the structure, leaving the active accessible when the purpose of encapsulation is to make it inaccessible. In other embodiments, however, all or a portion of the cross-linking occur prior to introduction of the active.

The delivery systems disclosed herein are operable to be used in a variety of applications. The applications discussed below are representative and illustrative, though certainly not all-inclusive. Suitable actives for use in the various applications are also provided below.

In one embodiment, at least one substrate (e.g., yarn, yarn precursor, thread, filament, fiber) is used to form a fabric or a textile. In certain embodiments, the fabric or the textile formed with the yarn, yarn precursor, thread, filament, or fiber includes both the medicated yarn of this disclosure along with an ordinary, non-medicated yarn, yarn precursor, thread, filament, or fiber. For example, in woven textiles, the warp is operable to be traditional yarn and the weft is operable to be yarn of the present embodiments. In other embodiments, only medicated yarn, yarn precursor, thread, filament, or fiber is used.

Additional details about the substrate, actives, and/or method of forming the fabric or the textile are found in U.S. Pat. Nos. 9,669,012 and 10,799,464, U.S. Patent Publication Nos. 20170231919, 20190038568, and 20200390720, and U.S. patent application Ser. No. 17/678,612, each of which is incorporated herein by reference in its entirety.

In a preferred embodiment, the delivery device includes at least one conductive and/or electromagnetic yarn, yarn precursor, thread, filament, and/or fiber. The at least one conductive and/or electromagnetic yarn, yarn precursor, thread, filament, and/or fiber is formed of stainless steel, copper, aluminum, gold, silver, tungsten, iron, titanium, chromium, platinum, palladium, and/or nickel. In one embodiment, the at least one conductive and/or electromagnetic yarn, yarn precursor, thread, filament, and/or fiber is formed using at least one layer of electrically conductive ink. In one embodiment, the at least one layer of electrically conductive ink is cured using heat (e.g., 40-140° C.), UV irradiation, IR irradiation, and/or photonic curing. In a preferred embodiment, the electrically conductive ink is washable.

In one embodiment, the at least one conductive and/or electromagnetic yarn, yarn precursor, thread, filament, and/or fiber includes at least one active compound. Alternatively, the at least one conductive and/or electromagnetic yarn is incorporated into a fabric, textile, and/or delivery device with at least one yarn, yarn precursor, thread, filament, and/or fiber including the at least one active compound. In one embodiment, the at least one conductive and/or electromagnetic yarn, yarn precursor, thread, filament, and/or fiber is used to form a knitted textile or fabric. In another embodiment, the at least one conductive and/or electromagnetic yarn, yarn precursor, thread, filament, and/or fiber is used to form a woven textile or fabric.

In one embodiment, the delivery device is selectively activatable. In one embodiment, the delivery device is selectively activatable by turning the delivery device on and/or off. In one embodiment, the delivery device includes a power button or switch operable to turn the delivery device on and/or off. In one embodiment, the delivery device is operable to adjust parameters (e.g., voltage and/or temperature) on the delivery device (e.g., via a slider, via a selectable "heat" level). In one embodiment, the delivery device is operable to transmit information to the remote device and/or the remote server. Alternatively, the delivery device is adjustable without transmitting information to a remote device and/or a remote server.

In one embodiment, the delivery device incorporates at least one body sensor and/or at least one environmental sensor. In one embodiment, the delivery device is operable to transmit biometric data and/or environmental data to the remote device and/or the remote server. In one embodiment, the delivery device is operable to receive biometric data and/or environmental data from the remote device and/or the remote server. Alternatively, the delivery device is adjustable without transmitting information to and/or receiving information from a remote device and/or a remote server.

In one embodiment, the delivery device is selectively activatable via the remote device. In one embodiment, the remote device is operable to adjust parameters (e.g., voltage and/or temperature) on the delivery device (e.g., via the user interface of the remote device).

In one embodiment, the system does not include at least one body sensor. In one embodiment, the system does not include at least one environmental sensor. In one embodiment, the system does not include a remote device. In one embodiment, the system does not include a remote server. In one embodiment, the delivery device (e.g., including the at least one conductive and/or electromagnetic yarn, yarn precursor, thread, filament, and/or fiber) is functional without interaction with at least one body sensor, at least one environmental sensor, a remote device, and/or a remote server.

Figures 2, 3:
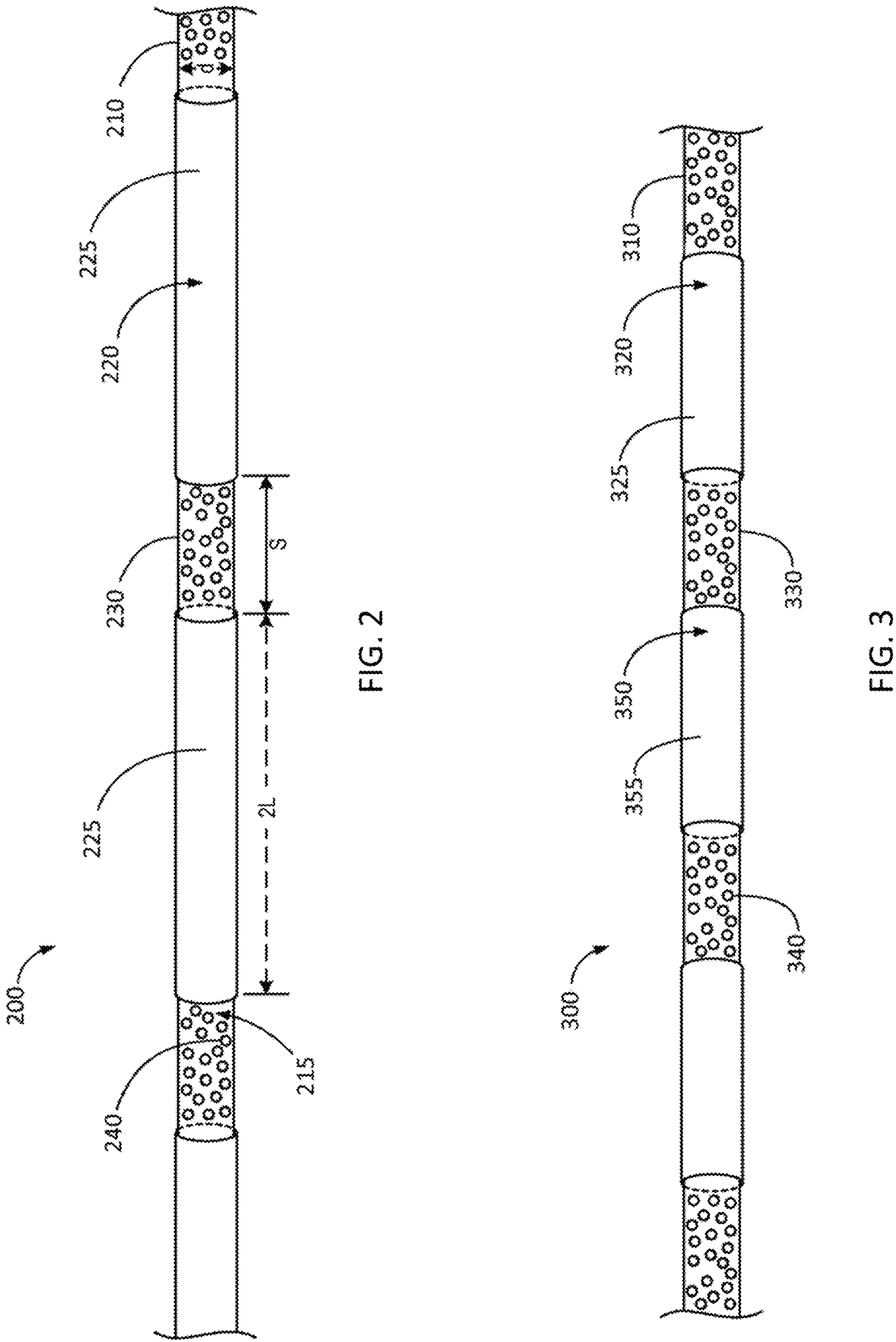
FIG. 2 is a perspective view of an embodiment of an intermittently coated yarn including a single type of coating.
FIG. 3 is a perspective view of an embodiment of an intermittently coated yarn including two types of coatings.

Shown in FIG. 2 is an embodiment of a drug delivery system 200 of the present disclosure operable to be included in the delivery device. As can be appreciated, although much of the disclosure and Figures may refer to or depict a yarn, other substrates (e.g., yarn precursors, threads, fibers, etc.) are also operable to be used in an analogous manner. The drug delivery system 200 includes the yarn, yarn precursor, thread, filament, fiber, or substrate, which is also operable to be referred to as the core 210 of the drug delivery system 200. A polymer (e.g., elastomer) is operable to be incorporated into or loaded onto the core 210 to form a polymeric (e.g., elastomeric) matrix 215, which may also be referred to as an inner matrix, inner polymer matrix, or drug matrix. The core 210 is also operable to include active compounds or particles 240 that are dispersed and/or immobilized in the polymer (e.g., elastomer) matrix 215 of the core 210. In certain embodiments, the polymer (e.g., elastomer) and/or the active 240 is applied to the core 210 of drug delivery system 200. Segments of the core 210 are operable to be coated, partially coated, or uncoated. In particular embodiments, the core 210 of the drug delivery system 200 is operable to be partially, selectively, or intermittently coated along the longitudinal axis or length of the core 210. For example, as illustrated in FIG. 2, the core 210 is operable to be intermittently coated with a coating 220 that is impermeable or substantially impermeable to the active 240 in the inner polymer matrix 215. Because the coated or occluded segments 225 of the core 210 are impermeable or substantially impermeable to the active 240 loaded into the drug delivery system 200, they are also referred to herein as "occluded" segments. In one embodiment, the core 210 similarly includes exposed, uncoated, non-occluded, or "open" segments 230, which are permeable to the active 240.

As is also shown in FIG. 2, the coated or occluded segments have a length of 2 L, while the uncoated or non-occluded segments have a length of S. The diameter of the core is represented by d. In one embodiment, the occluded segments 225 are operable to be configured such that the ratio of 2 L/d is larger than about 5, larger than about 10, or larger than about 25. Similarly, the ratio 2 L/S of adjacent occluded and non-occluded segments (225, 230, respectively) is operable to be greater than about 1, greater than about 4 (corresponding to 80% occlusion, 20% open), or greater than about 9 (corresponding to 90% occlusion, 10% open). Adjacent occluded and non-occluded segments are operable to refer to segments that are next to each other along the longitudinal axis of the yarn or core 210. In certain embodiments, the drug delivery system 200 are operable to be configured such that the lengths 2 L and S of occluded and non-occluded segments (225, 230, respectively) are substantially constant or uniform along the length or longitudinal axis of the yarn or core 210. In other embodiments, the lengths 2 L and S of occluded and non-occluded segments (225, 230, respectively) are operable to be varied along the length or longitudinal axis of the yarn or core 210.

Referring to FIG. 3, in certain embodiments of a drug delivery system 300 operable to be included in the delivery device, more than one type of occluded segment 325, 355 is operable to be provided. For example, the core 310 is operable to be coated with a first coating 320 and a second coating 350, each of which is operable to be impermeable, substantially impermeable, or semi-permeable to the active 340. Additional coatings with various functional and physical properties are also operable to be employed (e.g., a third coating, fourth coating, etc.). Coatings 320 and 350 are operable to be configured in any suitable arrangement. For example, they are operable to be adjacent to each other or they are operable to be separated by a non-occluded segment 330, or a combination thereof. In certain embodiments, coatings 320 and 350 are operable to be arranged such that moving axially along the length of the yarn or core 310, one would encounter segments alternating between two or more polymer coatings (e.g., polymer A and polymer B). Uncoated segments 330 are also operable to be included as part of the arrangement. As described more fully below, the pattern and sizing of the coated segments are operable to be selected to control the rate of release of the active 340 from the drug delivery system 300 over time.

In particular embodiments, the coatings 320 and 350 are operable to include different materials with different properties. For example, the coatings 320 and 350 are operable to contain polymers having different properties that will affect the rate of release of active 340. For example, in one embodiment, polymer B is more soluble in water or other aqueous milieu than polymer A, so that the release rate of the active 340 is relatively low until faster release is "triggered" or commenced by exposure to water (e.g., one or more launderings or rinses, or sweat) that breaks down or degrades the polymer B segments to expose the active-containing core 310. Such degradable materials are known in the art, such as water-soluble polymers, poly-lactic acid, poly-L-lactide, poly-glycolic acid and their copolymers, as well as other polyesters, polycaprolactone, biopolymers such as those based on collagen or gelatin or other peptides, certain natural gums, certain polysaccharides, chitosan and derivatives, and derivatives and mixtures thereof. Other erodible or biodegradable polymers are also operable to be used.

In other embodiments, two different polymers that are each impermeable to a different type of active compound 340 are operable to be used and arranged in a manner that controls the rate of release of each of the different active compounds 340. Furthermore, in additional embodiments, three or more coatings (e.g., polymers A, B and C) are also operable to be used and arranged in a variety of configurations (e.g., alternating) and with or without uncoated segments.

Figure 4:
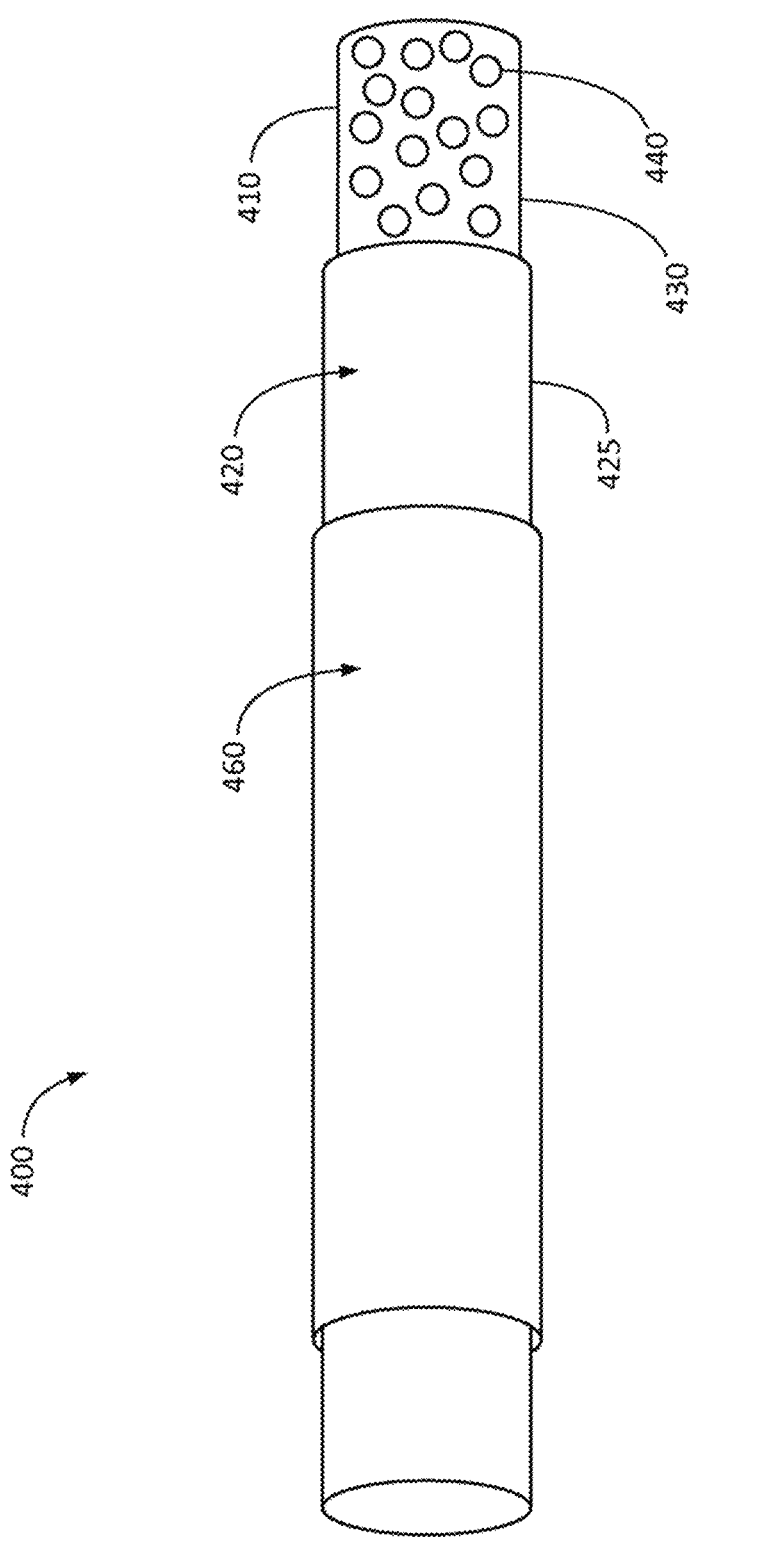
FIG. 4 is a perspective view of an embodiment of a yarn including an outer sheath or coating.

Referring to FIG. 4, a drug delivery system 400 operable to be included in the delivery device is shown having an outer sheath 460 that covers both the occluded segments 425 (i.e., covered with a coating 420) and open segments 430 of the yarn or core 410. The outer sheath 460 is operable to cover the entire length of the yarn or substrate 410, or one or more selected portions thereof. In some embodiments, the outer sheath 460 includes a material that breaks down or degrades over time or upon exposure to a "trigger" or particular event (e.g., exposure of a water-soluble sheath to water or sweat), thereby leaving the underlying yarn or substrate including coated and/or uncoated segments (425, 430, respectively) as described above. In some of such embodiments, the outer sheath 460 is operable to be impermeable or substantially impermeable to the active 440 such that it prevents release of the active 440 until a "trigger" event, at which point the release rate is operable to be controlled by the arrangement of the coated and uncoated segments (425, 430, respectively) underlying the outer sheath 460. The presence of the outer sheath 460 is operable to provide additional adjustments to the desired release of the active 440 over time, including the potential for controlled or delayed release of the active 440 from the drug delivery system 400.

Various materials are operable to be used to prepare the polymeric or inner or protective matrix of the drug delivery system. For example, the matrix is operable to include a polymer or an elastomer that exhibits relatively low toxicity, low allergenic potential, and/or low skin irritation. The matrix also is operable to release the active at a rate that delivers an efficacious and reasonably safe dose in the time anticipated or desired for the drug delivery system-tissue contact. Additional details regarding the matrix are found in U.S. Patent Publication No. 20200390720, which is incorporated herein by reference in its entirety.

In some embodiments, the "coating" or "sheath" materials that occlude the active-in-matrix dispersion in the embodiments of this disclosure are of low permeability or impermeable to the active. Many commercial coatings well known to one skilled in the art are operable to be used, with consideration to surface interactions. The coating is operable to be inorganic or organic, or a combination of, for example, inorganic particles or laminates bound together with an organic polymer as binder. The coating is operable to be an inorganic coating, such as a composition of zinc oxide (e.g., 93% zinc oxide), as used in an example provided herein. The coating is also operable to be selected from an organic polymer.

Low permeability is often be associated with a highly crystalline polymer, though high crystallinity is not necessarily required if the polymer is in the glassy state near ambient temperatures. In some embodiments, polymers of low crystallinity that nonetheless have high tenacity and low permeability to one or more actives are operable to be used as coatings.

In other embodiments, the coating material includes a high-crystallinity thermoplastic polymer and is processed thermoplastically. In certain embodiments of the present disclosure, the melting temperature of the coating polymer is low enough to allow processing at temperatures that are low enough to limit thermal degradation of the active. Coating materials are operable to be purchased commercially or are operable to be prepared by dissolving the desired polymer in a suitable solvent. Exemplary polymers for use as coating materials include polypropylene, polyvinyl chloride, PTFE (non-porous), polyvinylidene fluoride (PVDF), PMMA, shellac, polycarbonate (e.g., Lexan), polybutylene terephthalate, epoxy, polyethylene terephthalate (PET), high-density polyethylene, nylon, polyimide, celluloid, acrylonitrile butadiene styrene (ABS), phenol-formaldehyde resin, and polystyrene. Additional details regarding coatings compatible with the present invention are described in U.S. Patent Publication No. 20200390720, which is incorporated herein by reference in its entirety.

In one embodiment, the at least one substrate includes at least one first substrate and at least one second substrate. The at least one first substrate includes at least one active composition and the at least one second substrate does not include at least one active composition. For example, a first yarn or filament includes a capsacinoid and a second yarn or filament does not include an active composition (i.e., is non-medicated). A fabric or textile is formed from the first yarn and the second yarn (e.g., knitted, woven, etc.).

In another embodiment, the at least one first substrate includes at least one first active composition and the at least one second substrate includes at least one second active composition. Advantageously, this embodiment allows for at least two active compositions. Further, the at least one first active composition and the at least one second active composition are operable to have different desired release rates. This embodiment allows for modifying the desired release rates of the at least one first active composition and the at least one second active composition by varying factors including, but not limited to, an occlusion percentage; a loading dose; a particle size of the at least one active composition (e.g., a range of particle sizes); the polymer, oligomer, and/or monomer matrix; and/or the at least one coating. For example, but not limitation, a textile is formed with a first yarn and a second yard. The first yarn includes a first active composition with a first occlusion percentage; a first loading dose; a first particle size of the at least one first active composition (e.g., a range of particle sizes); a first polymer, oligomer, and/or monomer matrix; and at least first one coating. The second yarn includes a second active composition with a second occlusion percentage; a second loading dose; a second particle size of the at least one second active composition (e.g., a range of particle sizes); a second polymer, oligomer, and/or monomer matrix; and at least one second coating.

While the examples described above include a first substrate and a second substrate, the present invention is not limited to two substrates. In one embodiment, the fabric or the textile includes a plurality of substrates. Each of the plurality of substrates is operable to include at least one active composition. In one embodiment, one or more of the plurality of substrates does not include at least one active composition. For example, but not limitation, a textile is formed with a first yarn, a second yarn, a third yarn, and a fourth yarn. The first yarn includes a first active composition; the second yarn includes a second active composition; the third yarn includes the first active composition, the second active composition, and a third active composition; and the fourth yarn does not contain an active composition. As one of ordinary skill in the art will understand, the factors listed above are operable to be manipulated to achieve a desired release profile.

In one embodiment, the textile formed with the yarn or filament is a knitted textile. In one embodiment, the knitted textile is a circular knit. Alternatively, the knitted textile is a flat knit. In one embodiment, the knitting of the textile is facilitated by treating the yarns of the present disclosure with a lubricant (e.g., 2% to 3% lubricant) prior to knitting.

Advantageously, the knitted textile is operable to provide both a relaxed state and a stretched stated. In one embodiment, the wearable article or garment is formed of the knitted textile. In a preferred embodiment, the wearable article or garment is operable to substantially conform to at least one body part of a wearer. The at least one body part includes, but is not limited to, a finger, a hand, a wrist, an elbow, an arm, a shoulder, a torso, a head, a face, a neck, a toe, a foot, an ankle, a knee, a hip, and/or a leg. In one embodiment, the wearable article or garment is operable to provide compression to the at least one body part of the wearer. In one embodiment, the wearable article or garment is seamless. Advantageously, a seamless wearable article or garment provides additional comfort to a wearer by reducing points of friction.

In one embodiment, the at least one delivery device formed with the yarn or filament is a knitted textile. In one embodiment, the knitted textile is a circular knit. Alternatively, the knitted textile is a flat knit. In one embodiment, the knitting of the textile is facilitated by treating the yarns of the present disclosure with a lubricant (e.g., 2% to 3% lubricant) prior to knitting.

Advantageously, the knitted textile is operable to provide both a relaxed state and a stretched stated. The at least one delivery device is preferably a wearable article or garment. In one embodiment, the wearable article or garment is formed of the knitted textile. In a preferred embodiment, the wearable article or garment is operable to substantially conform to at least one body part of a wearer. The at least one body part includes, but is not limited to, a finger, a hand, a wrist, an elbow, an arm, a shoulder, a torso, a head, a face, a neck, a toe, a foot, an ankle, a knee, a hip, and/or a leg. In one embodiment, the wearable article or garment is operable to provide compression to the at least one body part of the wearer. In one embodiment, the wearable article or garment is seamless. Advantageously, a seamless wearable article or garment provides additional comfort to a wearer by reducing points of friction.

In some embodiments, the substrate is a yarn, yarn precursor, thread, filament, fiber, textile, or fabric. In certain embodiments, the yarn includes a nylon, polyester or acrylic material. In one embodiment, the wearable article forms an orthopedic cast, splint material, a wound dressing, socks, hats, face/ski masks, scarves, tiaras, chokers, skullcaps, undergarments, skin guards, wrist bands, arm bands, knee pads, bras, shirts, leggings, nylon stockings, athletic supporters, robes, neck bands, head bands, ear muffs, gloves, diapers, poultices, facial masks, paraffin gloves, joint braces, pillowcases, blankets, sheets, and furniture coverings. In one embodiment, the present invention provides a wearable article including, but not limited to, an ankle sleeve, an arm sleeve, a calf sleeve, a knee sleeve, a lower leg sleeve, a wrist sleeve, a shirt or a partial shirt, pants or partial pants, leggings or partial leggings (e.g., 7/8 leggings, capri, shorts), a sock, or a glove. In one embodiment, the wearable article is a brace including, but not limited to, an ankle brace, an arm brace, a knee brace, a lower leg brace, a wrist brace, a finger brace, a shoulder brace, a neck brace, a back brace, or a hip brace. In one embodiment, the wearable article is a splint including, but not limited to, an ankle splint, an arm splint, a knee splint, a lower leg splint, a wrist splint, a finger splint, a shoulder splint, a neck splint, a back splint, or a hip splint.

In one embodiment, the wearable article is unitarily formed from the textile, the fabric, or the substrate. In one embodiment, the wearable article is operable to be pulled onto the at least one body part. For example, but not limitation, a knee sleeve is operable to be pulled over the foot and the calf, and placed over the knee. In another example, a shirt is operable to be pulled over the head, and arms of the wearer pulled through sleeves of the shirt.

In still another embodiment, the wearable article is operable to be wrapped around the at least one body part. For example, but not limitation, the wearable article is a back brace operable to secure around a torso of a wearer. In another example, the wearable article is an elastic bandage (e.g., ACE bandage) operable to wrap around the at least one body part (e.g., arm, leg).

In another embodiment, the textile, the fabric, or the substrate forms a layer in the wearable article. For example, and not limitation, in one embodiment, the textile, the fabric, or the substrate forms a first layer of the wearable article in contact with surface of the skin (e.g., a lining) and a second layer of the wearable article is exposed to the environment.

In certain embodiments, the yarn or substrate requires greater elasticity or stretch. Thus, in one embodiment, the yarn is plied or twisted with an air-covered yarn (e.g., spandex) to enable additional stretch of the yarn. Additionally, the yarn is operable to be air-covered/air-intermingled (i.e., blowing air onto the yarn and adding a spandex core into the middle of the yarn). These methods are particularly useful for garments that need a lot of stretch such as tights, leggings, or an elastic portion on a top of a sock or an ankle sleeve. In one embodiment, the wearable article is operable to stretch to conform to the at least one body part of a wearer.

In one embodiment, the secondary yarn is wrapped or covered with filaments (e.g., nylon filaments) to make a fibril. A plurality of fibrils is combined to form a yarn. In one embodiment, the yarn is a multi-component, rope like structure with a plurality of interstitial spaces. The yarn is operable to be passed through a trough containing a polymer, oligomer, or monomer matrix, which fills the interstitial spaces. Additionally, some of the polymer, oligomer, or monomer matrix remains on a surface of the yarn. The wetted yarn is polymerized (e.g., via UV polymerization). The polymerized yarn hardens the polymer, oligomer, or monomer matrix. While the overall texture and elasticity of the polymerized yarn is changed relative to the original yarn, the polymerized yarn remains elastic and is operable to stretch.

In one embodiment, the delivery device is a wearable article. In one embodiment, the wearable article further includes at least one closure mechanism. The at least one closure mechanism includes, but is not limited to, at least one strap, at least one snap, hook and loop tape, at least one tie, at least one buckle, at least one zipper, at least one lace, at least one closure system (e.g., BOA fit system), at least one latch, at least one hook, at least one elastic, at least one adhesive, at least one fastener, and/or at least one clip. In one embodiment, the at least one closure mechanism allows for customization of fit of the wearable article to the wearer. In another embodiment, the at least one closure mechanism secures the wearable article to at least one body part of the wearer. For example, but not limitation, hook tape and loop tape secure a wrist brace to a wrist of a wearer. In another example, the at least one closure mechanism is a tie to secure pants to a waist of a wearer. In still another example, at least one hook or at least one clip secures an elastic bandage (e.g., ACE bandage) to the at least one body part (e.g., arm, leg).

In one embodiment, the present invention provides an article (e.g., non-wearable article) that is operable to release at least one active composition. In one embodiment, the article is formed using yarns, yarn precursors, threads, filaments, fibers, textiles, and/or substrates (e.g., films, sheets, patches, cut and sew pieces) that are operable to persistently release the at least one active composition. Advantageously, the article and/or the yarns, yarn precursors, threads, filaments, fibers, textiles, and/or substrates are operable to persistently release the at least one active composition after at least one wash cycle. In one embodiment, the yarns, yarn precursors, threads, filaments, fibers, textiles, and/or substrates form a knitted structure. Advantageously, the knitted structure is operable to provide both a relaxed state and a stretched state. In one embodiment, the article is formed of the knitted structure. Alternatively, the yarns, yarn precursors, threads, filaments, fibers, textiles, and/or substrates form a woven structure. In one embodiment, the yarns, yarn precursors, threads, filaments, fibers, textiles, and/or substrates are operable to be used for cut and sew. The article is operable to contact at least one body part of a user. In one embodiment, the article is operable to substantially conform to the at least one body part of a user. The at least one body part includes, but is not limited to, a finger, a hand, a wrist, an elbow, an arm, a shoulder, a torso, a head, a face, a neck, a toe, a foot, an ankle, a knee, a hip, and/or a leg. In one embodiment, the article is seamless. Advantageously, a seamless article provides additional comfort to a user by reducing points of friction. In an alternative embodiment, the article or garment is formed of a woven textile.

In one embodiment, the article includes a towel, a cover, a pillowcase, a sheet (e.g., flat sheet, fitted sheet), a pad (e.g., mattress pad), a comforter, a blanket, upholstery, a mat (e.g., yoga mat, exercise mat, anti-fatigue mat), a grip (e.g., athletic equipment, handlebars), and/or a sleeping bag or sleeping bag liner. In one embodiment, the cover includes a seat cover, an electric device cover (e.g., mouse cover, keyboard cover, phone cover), a heating pad cover, a duvet cover, ice pack cover, steering wheel cover, a furniture cover, and/or an exercise apparatus cover (e.g., bench cover). In one embodiment, the article is an upholstered article.

In one embodiment, the delivery device further includes at least one printed circuit board (PCB). The at least one PCB is preferably formed of a flexible material including, but not limited to, a polyimide and/or a polyester. In one embodiment, the at least one PCB includes at least one processor, at least one memory, a communications interface (e.g., BLUETOOTH®), a heater or heating device, and/or a battery. In one embodiment, the battery is rechargeable. Each delivery device preferably includes a unique device identification (ID) number. Additionally, each delivery device includes data related to the at least one active compound.

In one embodiment, the at least one PCB is stored in a pocket or pouch incorporated into the delivery device. In one embodiment, the at least one PCB is removable. Alternatively, the at least one PCB is water resistant and/or waterproof.

An overview of various classes of conditions and treatments that are operable to utilize the various embodiments of the present disclosure are described below.

For application of actives to portions of skin suffering from abnormalities or for cosmetic improvement, the present embodiments offer direct skin contact, localizable coverage, washing machine compatibility ("washability"), rapid rate of release, continuous coverage through the night if desired or, as a patch, throughout the day or night. An example of an active for particular skin conditions includes tea tree oil for acne, eczema, psoriasis, etc. In addition to acne, other skin conditions for which the embodiments described here are particularly useful include rashes, skin allergies, folliculitis, impetigo, erysipelas, cellulitis, and dermatitis.

In applications that are considered therapeutic, cosmeceutic, cosmetic, etc., embodiments of the present disclosure are operable to improve skin condition and appearance via the release of, for example, vasodilators, rubefacients, ceramide, emollients, dermoprotective, lipolytic, or epithelializing compounds.

The embodiments described herein are operable to be of particular utility in medication- or antimicrobial-releasing socks, because socks must be washed so frequently, and the need is inherently high due to the relatively high rate of foot- and sock-related disorders, risks, and inconveniences, such as offending odors and the associated risks of infections (not only bacterial but also fungal and viral), and more serious risks faced by the growing incidence of diabetes.

In addition to acne, eczema and psoriasis, the following conditions are treatable, or preventable, with embodiments of the present disclosure: scleroderma (which often leads to Raynaud's syndrome), neutrophilic dermatosis, urticaria, xeroderma-pigmentosum, Goltz syndrome, recessive dystrophic epidermolysis bullosa, Harlequin ichthyosis, hypertrichosis, Morgellons disease, dermatofibrosarcoma protuberans, and infections such as human papilloma virus (HPV). Scleroderma may occur in both non-systemic and systemic forms, and while the delivery systems of the present disclosure are operable to be suited for treating the non-systemic form (e.g., with a fabric that would release an active oil extract from *Salvia* miltiorrhiza (Danshen) and/or from *Capparis spinosa*), they are effective against the systemic form as well. *Salvia* miltiorrhiza and *Capparis spinosa* work against scleroderma in two distinct mechanisms, so that delivery of a combination of the two oils via the delivery systems of the present disclosure are operable to be particularly efficacious.

In addition, delivery systems of the present disclosure are operable to provide for wound dressings that are non-adherent, non-occlusive for oxygen transport, and non-irritating. Wounds for which the systems are operable to be used include chronic wounds, such as malignancies, persistent infections (e.g., gangrene), decubitis, diabetic ulcers, and other ulcers of traumatic, venous, or ischemic origin. While the delivery system is operable to be used as a primary dressing, it is also operable to be effective as a secondary dressing, delivering medicament through the primary dressing.

In one embodiment related to wound dressing, a delivery system of the present disclosure is operable to be used as an insert or lining to a cast, splint, sling, or brace. There are over 6.8 million broken bones just in the U.S. every year, many requiring the use of a cast, splint, sling, or brace for treatment. In the case of individuals treated for scoliosis, for example, patients must wear a full body cast and lie in bed for 3 to 6 months. There are many common negative issues associated with wearing casts for prolonged periods of time, including but not limited to, allergic reactions, skin sores, infections, joint stiffness, muscle loss, offensive odor, burns, and compartment syndrome, which greatly limits blood flow. Many or all of these negative side effects are operable to be effectively treated or mitigated by delivery of appropriate actives via the systems of the present disclosure. In one embodiment, such an application employs the disclosed systems in the form of an insert or lining to a cast, splint, sling, or brace. In one embodiment, the cast/insert system is designed such that the insert is operable to be removed (e.g., daily, if necessary) for washing without interfering with the supportive and protective functions of the cast or brace. The insert is operable to provide release of antimicrobials, growth factors, analgesics, and/or skin toning/cosmeceutical actives, and operable to release medicaments or essential oils designed to increase blood circulation. Several classes of actives are beneficial for treatment of wounds and are operable to be used with the systems of the present disclosure including, but not limited to, growth factors, clotting factors, local anesthetics, steroids, vitamins, minerals, antimicrobials, or (e.g., in milder wounds) antiseptics and bacteriostats.

Delivery systems of the present disclosure are operable to deliver sleep-/relaxation-aiding actives both into the bloodstream through release into the skin, and into the brain through the trigeminal neural pathway via nasal inhalation. Many compounds and oils from nature that induce relaxation often have analgesic action as well. Thus, due to action by these substances at one or more opioid receptors, embodiments of the disclosure are operable to be applied to release these actives and—potentially with combined transdermal and trigemical (inhalation) delivery routes—achieve a synergistic combination of anxiolytic and analgesic actions. In one embodiment, the present invention includes a combination of two actives. In one embodiment, the combination of two actives is a combination of lavender and Melissa essential oils. Plant essential oils that are purported analgesics include lavender, wintergreen, Roman chamomile, marjoram, peppermint, rosemary, thyme, vetiver, helichrysum, ginger, lemongrass, copaiba (copal), and balsam fir. Specific fractions or components of these oils, such as menthol, are operable to be used as well, particularly if they have substantial volatility. In some embodiments, the vapor pressure of the active at 35° C., for inhalation/trigeminal neural pathway delivery, is equal to or greater than about 0.01 Torr, greater than about 0.1 Torr, or greater than about 0.5 Torr. A drug with lower vapor pressure than this may still be practical if the potency of the drug is very high, such as with carfentanil.

Extracts and purified compounds from the following plants have been reported in the literature to have central-acting analgesic activity, and these are operable to be incorporated into the various embodiments of the present disclosure for relief of pain and, in many cases, for relaxation as well: *Abutilon indicum, Acacia ferruginea, Acacia nilotica, Achillea ageratum, Acicarpha tribuloides, Aconitum carmichaelii, Aconitum flavum, Aconitum japonicum, Acorus calamus, Adansonia digitata, Afrormosia laxiflora, Agastache sinense, Ageratum conyzoides, Albizia lebbek, Alhagi maurorum, Aloe vera, Amelanchier ovalis, Anacardium occidentale, Anchomanes difforms, Annona squamosal, Apium graveolens, Araujia sericifera, Astragalus siculus, Baphia nitida, Berlinia grandiflora, Brassica rapa, Buddleja cordata, Bupleurum chinense, Cadia rubra, Caesalpinia ferrea, Calotropis procera, Cannabis sativa, Canthium parviflorum, Caralluma tuberculata, Carthamus tinctorius, Cedrus deodara, Celastrus paniculatus, Centella asiatica, Chasmanthera dependens, Chelidonium majus, Chrozophora verbascifolia, Cinnamomum zeylanicum, Citrullus colocynthis, Clematis chinensis, Cleome viscose, Clerodendrum infortunatum, Clitoria ternatea, Cocculus pendulus, Commiphora molmol, Cordia francisci, Cordia martinicensis, Cordia myxa, Cordia ulmifolia, Cucumis trigonus, Culcitium canascens, Curcuma zedoaria, Cuscuta chinensis, Cyathea nilgirensis, Cymbopogon schoenanthus, Cystoseira usneoides, Datisca cannabina, Desmodium canadense, Dioclea grandiflora, Diodia scandens, Dolichos falcatus, Ducrosia ismaelis, Egletes viscosa, Elaeagnus kologa, Elaeocarpus canitrus, Eriobotrya bengalensis, Ervatamia coronaria, Eryngium foetidum, Eucalyptus camaldulensis, Euphorbia hirta, Fagraea racemosa, Ficus glomerata, Foeniculum vulgare, Ganoderma lucidum, Genista patens, Glaucium flavum, Harpagophytum procumbens, Hedera rhombea, Heracleum hemsleyanum, Hibiscus sabdariffa, Himanthalia helongata, Himulus lupulus, Hypericum calycinum, Hypericum perforatum, Inula crithmoides, Inula viscosa, Ipomoea leari, Irvingia gabonensis, Juniperus oxycedrus, Laminaria achroleuca, Lantana camara, Lawsonia inermis, Ledebouriella seseloides, Lepidium sativum, Leucas aspera, Leucojum aestivum, Ligusticum sinense, Lippia alba, Lippia geminate, Luvunga scandens, Lycopodium clavatum, Lysimachia christinae, Maesa ramentacea, Melaleuca elliptica, Melaleuca styphelioides, Mentha piperita, Mikania cordata, Morinda citrifolia, Morus alba, Mucuna pruriens, Myrica nagi, Myrtus communis, Nepeta caesarea, Nepeta italica, Neurolaena lobata, Nigella sativa, Nyctanthes arbor-tristis, Ocimum sanctum, Oplopanax elatus, Origanum onites, Paeonia moutan, Panax ginseng, Pancratium maritimum, Paullinia cupana, Peganum harmala, Persea Americana, Photinia serrulata, Phyla nodiflora, Phyllanthus niruri, Phyllanthus sellowianus, Phyllanthus tenellus, Phyllanthus urinaria, Pimpinella anisum, Pinus koraiensis, Piper abutiloides, Piper cincinnatoris, Piper lindbergii, Piper longum, Piper methysticum, Piper umbellatum, Piscidia erythrina, Platycodon grandiflorum, Polygala cyparissias, Polypodium vulgare, Pongamia pinnata, Portulaca grandiflora, Portulaca oleracea, Prunus spinosa, Psammosilene tunicoides, Psidium pohlianum, Psychotria brachypodia, Psychotria colorata, Pterocarpus indicus, Ptychopetalum olacoides, Pycnocomon rutaefolia, Quercus infectoria, Quercus lineata, Randia siamensis, Ranunculus japonicas, Rhamnus procumbens, Rhazya stricta, Ricinus communis, Roylea elegans, Salvia haematodes, Santolina chamaecyparissus, Saussurea involucrate, Scabiosa atropurpurea, Senna italic, Serjania communis, Sida cordifolia, Sideritis mugronensis, Siphocampylus verticillatus, Stephania dinklagei, Stefania wightli, Strychnos nux-vomica, Synedrella nodiflora, Tabebuia chrysotricha, Tabernaemontana pandacaqui, Tamarix milotica, Taraxacum officinale, Teclea nobilis, Tecomella undulate, Teucrium carthaginense, Theobroma leiocarpa, Thymus vulgaris, Tillandsia usneoides, Tinospora cordifolia, Tinospora crispa, Torresea cearensis, Trachelospermum jasminoides, Trema guineensis, Trianthema portulacastrum, Tribulus terrestris, Trichilia catigua, Trigonella anguina, Trigonella foenum-graecum, Typhonium giganteum, Urtica dioica, Valeriana jatamansi, Vernonia condensate, Viola mandshurica, Vitex negundo, Zingiber officinale,* and *Ziziphus jujube.*

The dissolution-limited embodiments of the present disclosure are operable to involve the use of a solid active ingredient as the active compound. One skilled in the art will recognize that, in many cases, the individual purified components of essential oils are often solids near ambient (room) temperature. For example, the liquid known as peppermint essential oil has as its predominant component menthol, which is a solid at room temperature. Menthol typically constitutes 50% to 80% of peppermint oil. As a further example, in a case where peppermint oil includes 70% menthol, the menthol component is accompanied by 30% of "other ingredients." One of ordinary skill will understand that these other components are generally quite similar in molecular structure to menthol, but different enough that these minor ingredients act to lower the melting point of the menthol. One of ordinary skill in the art will further understand that this melting point depression effect is common in plant oils, and means that many of the benefits from essential oils discussed in this disclosure in fact are operable to be achieved by solid actives, which are suited for the yarns and other substrates disclosed herein.

Fungal infections of the skin can be notoriously long-lasting, and compliance with an antifungal spray can be poor, for example, due to the need for daily application in the harried early morning time. An antifungal-medicated piece of clothing that is washable is operable to provide for long-term application to the site of infection without requiring any compliance on the part of the user, beyond the normal washing of the fabric that is required in any case. With, for example, 4 or 5 pairs of medicated socks, one could advantageously maintain continuous application of the active to the site during all waking hours of the day, and even at night if desired, without any conscious effort other than donning the designated socks each morning.

Vapor-releasing salves can be notoriously short-acting, and are not well suited for constancy of release. On the other hand, prior known patches are unsightly and even disfiguring. Advantageously, the embodiments of the present disclosure are operable to overcome these drawbacks by providing a sufficiently sophisticated delivery system for constancy of release which is nevertheless in the format of a fully functional (e.g., washable) article of clothing, such as a scarf, cap, veil, woven necklace, choker, neck band, ear muffs, or other headwear. Other applications that are operable to benefit from vapor release include trigeminal neuropathy, also known as "the suicide disease" due to the excruciating pain it causes. This condition is operable to be treated, for example, by using a delivery system disclosed herein that releases pain-numbing vapors such as menthol at a more constant rate than salves without requiring repeated applications every few hours. Other conditions treatable with such an approach include nasal congestion, emphysema, sarcoidosis, pleural effusion, pulmonary edema, pulmonary hypertension, pneumonia, tuberculosis, various infectious diseases, respiratory irritation (e.g., from breathing polluted air), and non-productive coughing.

Nutritional and nutraceutical compounds are also operable to be delivered transdermally according to embodiments of the present disclosure. Such compounds are operable to be delivered, e.g., via a transdermal patch or via everyday-use and other fabrics. Moreover, the large surface areas for transdermal delivery made possible by the delivery systems disclosed herein allow for delivery of larger doses than would be possible for traditional transdermal patches.

Considerable instruction is provided herein for producing washable, medicated materials for delivery of drug to the skin, which with many drugs translates into systemic delivery (i.e., transdermal delivery to the bloodstream). Nicotine, fentanyl, methylphenidate, scopolamine, nitroglycerine, rivastigmine, clonidine, Vitamin B12, estrogen and testosterone are some examples of drugs that are currently delivered transdermally through medicated patches, which are, of course, not washable, and thus must be discarded when dirty. Drugs requiring daily (or near-daily) application are operable to benefit from the embodiments described herein; for example, with children's attention-deficit/hyperactivity disorder (ADHD), exposure to dirt of all forms is of course to be expected for a (hyperactive) child, and a washable, reusable patch is an advantage. Furthermore, if the present disclosure is used in the form of an article of clothing, particularly one that is fairly tight-fitting such as a sock or cap, then it becomes possible to eliminate the need for adhesives, which are essentially required for traditional transdermal patches and present a range of practical issues (e.g., allergic reactions). The embodiments described herein are also operable to be used to deliver drugs systemically through mucosal membranes—a route known as transmucosal.

In some embodiments, resiniferatoxin, and related materials containing components of greater than 1 billion Scoville units, including extracts of *Euphorbia* species such as *Euphorbia resinifera* or *Euphorbia poissonii*, are used as active compounds. Such compounds are operable to be used in treating pain and/or other conditions.

It is within the scope of this disclosure for the "active" to be one that improves the quality of life through the steady release, even through many washes, of a pleasant and social aroma, including pheromones. The designs discussed elsewhere herein for promoting release into the air (discussed above in relation to inhalation-based delivery) are operable to be used for such an application. Many of the essential oils listed and discussed herein are well established as pleasing aromas or even as perfume components. Some embodiments discussed herein that yield a more nearly-constant release rate are operable to be used to create textiles, such as dresses and scarfs, which do not suffer from the relatively short action of a single application (spray) of perfume, and in fact do not require any action on the part of the customer or user.

Delivery of drugs and even some nutritional supplements to infants and toddlers can be a challenge due to swallowing/coordination limitations and taste intolerance. The delivery systems disclosed herein provide convenient products and methods for overcoming these delivery challenges, by incorporating medicament- or supplement-releasing embodiments of the disclosure into and onto commonly used (and frequently washed) items such as pacifiers, milk/formula bottles, stuffed animals, etc. Hydrophobic actives, in particular, will in general be released more rapidly into milk or formula than into water, and milk, particularly flavored milk, is operable to mask the taste of medicaments, providing for relatively high dilutions without increasing total fluid intake.

In another embodiment, gloves releasing circulation-improving compounds or oils (e.g., vasodilatory, rubifacient) and/or local anesthetic compounds for treatment or prevention of Raynaud's disease and related conditions are provided.

Certain embodiments also provide athletic garments and undergarments and other sportswear/active wear releasing one or more of the following: performance-enhancing actives; aspirin, local anesthetic, and/or capsaicin or a capsaicinoid for relief of pain or cold; creatine, glutamine, citrulline malate, beta-alanine, and/or branched-chain amino acids for muscle recovery or muscle stimulation; and handkerchiefs releasing cologne or perfume, antimicrobials, and/or vitamins.

In certain embodiments, solid active particles or powders (e.g., crystalline active particles) are used. Solid active particles (e.g., crystalline active particles) are operable to be used, in part, to better achieve dissolution-limited release kinetics. Exemplary forms of active compounds that are operable to be used include, but are not limited to, crystalline or polycrystalline solid particles, semi-crystalline solid particles, amorphous solid particles, plant extracts including crystalline or amorphous solid domains of one or more active compounds from the plant, and mixtures or combinations thereof. In further embodiments, the active compounds are operable to include components or fractions of plant essential oils, which may be crystalline at room temperature, and suitable for use. The term "plant essential oils" is as described in U.S. Patent Application Publication No. 2014/0271863, which is incorporated herein by reference in its entirety, and which also provides a listing of some of the organic compounds that provide for the desirable or therapeutic effects of these oils.

In some embodiments, the active includes a heating or cooling active. For example, in one embodiment, the active is selected from at least one of menthol, a menthol derivative, WS compounds (Wilkinson Sword™) (e.g., WS-3, 5, 12, and 23), methyl salicylate, ethyl salicylate, trolamine salicylate, capsaicin or a capsaicinoid, a synthetic heating or cooling agent (e.g., nonivamide), vanillyl butyl ether, ginger, eugenol, *kunzea, arnica*, camphor, niacinamide, and/or diphenyl hydramine. In certain embodiments, the active Other suitable actives include, but are not limited to, cannabidiol, BEAUPLEX® VH; ALL-Q® (coenzyme Q10) plus; coenzyme, SPECIKARE™ CQ10; ROVISOME™ Q10; SIGNALINE™ S, SERENITYL™ BIOFUNC-TIONAL; ATPEPTIDE™ IS; PROLIPID™ 141; VITAL ET™; GENTI-FOL® SA; CELLULINO®; lidocaine; SHA-PEPERFECTION™; FRESH'N™ CC menthol 50% (CY-CLOSYSTEM COMPLEX®); CARNIPURE™ CRYS-TALLINE; SYNIORAGE™ LS 9847; ULTRA FILLING SPHERES™; RONACARE® nicotinamide; VEXEL™ SP; cafeisilane C; ROVISOME™ caffeine; ISOCELL™ SLIM; DISILANOL C+™; SYNIORAGE™ LS 9847, N,N-Di-ethyl-meta-toluamide (DEET), picaridin, and/or melatonin. Other suitable actives are also within the scope of this disclosure (see, e.g., Table 1).

TABLE 1

| Skin Sensations | Skin Calming | Skin Energizing/Renewal | Skin Firming |
|---|---|---|---|
| Heat | Acne | Hydration | Anti-wrinkles |
| Cool | Irritation | Cellular Energy | Cellulite |
| Odor, Itch | Rosacea/Psoriasis | Protection | Anti-Glycation |
| Capsaicin | Emollients | Vitamins A, C and E | Carnosine |
| Nonivamide | Lidocaine | Glycolic Acid+ | Carnitine |
| Menthol | CoQ-10 | Resveratrol | Vitamin Bs, E & C |
| WS Derivatives | Cinnamates | Polyphenols | Peptides |
| Miconazole | Piroctone Olamine | Niacinamide | Salicylates |
| Diphenhydramine | Calamine | Glycyrrhizinic Acid+ | Alpha hydroxyl acids |
| | | Ergothioneine | |
| | | Ferulic Acid | |
| | | Caffeine | | includes a cooling component blend (e.g., isopulegol, menthyl lactate, menthoxypropanediol, and 2-isopropyl-N,2,3-trimethylbutyramide (WS-23)). Other suitable heating or cooling actives are also within the scope of this disclosure.

In various embodiments, the active includes an antifungal active. For example, in one embodiment, the active is selected from at least one of clotrimazole, miconazole, ketoconazole, terbinafine, fluconazole, and/or amphotericin. Other suitable anti-fungal actives are also within the scope of this disclosure.

In some embodiments, the active includes an antipruritic and/or skin calming active. For example, in one embodiment, the active is selected from at least one of an antihistamine (e.g., diphenhydramine or hydroxyzine), a corticosteroid (e.g., hydrocortisone), a counterirritant (e.g., mint oil, menthol, or camphor), and/or a local anesthetic (e.g., lidocaine, pramoxine, benzocaine, trolamine, calamine, coenzyme Q-10, or diphenyl hydramine). Other suitable antipruritic and/or skin calming actives are also within the scope of this disclosure.

In certain embodiments, the active includes an acne-treating active. For example, in one embodiment, the active is selected from at least one of an alpha-hydroxy acid (AHA) (e.g., glycolic acid or lactic acid), benzoyl peroxide, clay, salicylic acid, sulfur, tea-tree oil, azelaic acid, topical retinoid, and/or kojic acid. Other suitable acne-treating actives are also within the scope of this disclosure.

In various embodiments, the active includes an emollient. In one embodiment, the emollient is selected from at least one of shea butter, cocoa butter, a castor oil derivative, lanolin, squalene, coconut, jojoba, sesame, almond, another plant oil and/or butter, cetyl alcohol and derivatives, and/or a stearate. Other suitable emollients are also within the scope of this disclosure.

In one example, at least one delivery device (e.g., gloves, socks) includes a heating active (e.g., capsaicin, capsaicinoid). Based on biometric data and/or environmental data (e.g., temperature data from a body temperature sensor, an environmental temperature sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the heating active. Advantageously, this relieves a feeling of cold in the wearer. The at least one delivery device is also operable to decrease the voltage to the one or more of the at least one conductive and/or electromagnetic yarn, yarn precursor, thread, filament, and/or fiber based on the biometric data and/or the environmental data.

In another example, at least one delivery device (e.g., gloves, socks) includes a sleep aid (e.g., melatonin, magnesium). Based on biometric data (e.g., temperature data from a body temperature sensor, heart rate data from a heart rate sensor, respiration data from a respiration sensor, movement data from a movement sensor, brain wave data from a brain wave sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the sleep aid. Advantageously, this helps a wearer fall asleep or stay asleep. For example, and not limitation, a mobile application on the remote device is operable to include a sleep duration. In one embodiment, the clock in the at least one delivery device is operable to increase and/or decrease a rate of release based on the sleep duration. The at least one delivery device is also operable to decrease the voltage to the one or more of the at least one conductive and/or electromagnetic yarn, yarn precursor, thread, filament, and/or fiber based on the biometric data.

In yet another example, at least one delivery device (e.g., socks) includes an attention aid (e.g., caffeine, methylphenidate). Based on biometric data (e.g., movement data from a movement sensor, heart rate data from a heart rate sensor, EOG data from an EOG sensor, brain wave data from a brain wave sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the attention aid. Advantageously, this helps improve concentration in a wearer. The at least one delivery device is also operable to decrease the voltage to the one or more of the at least one conductive and/or electromagnetic yarn, yarn precursor, thread, filament, and/or fiber based on the biometric data.

In one example, at least one delivery device (e.g., socks) includes a muscle recovery or muscle stimulation aid (e.g., creatine, glutamine, citrulline malate, beta-alanine, branched-chain amino acids). Based on biometric data (e.g., analyte data from an analyte sensor (e.g., sweat sensor), location data from a location sensor (e.g., GPS), movement data from a movement sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the muscle recovery or muscle stimulation aid. Advantageously, this helps increase athletic performance (e.g., during training, during a race) and/or increase a rate of recovery in a wearer. For example, and not limitation, a mobile application on the remote device is operable to include a race length and/or a training duration. In one embodiment, the delivery device is operable to use GPS data (e.g., correlate with the race length) and increase a rate of release based on the GPS data. In one embodiment, the clock in the at least one delivery device is operable to increase a rate of release based on the training duration. The at least one delivery device is also operable to decrease the voltage to the one or more of the at least one conductive and/or electromagnetic yarn, yarn precursor, thread, filament, and/or fiber based on the biometric data.

In another example, at least one delivery device (e.g., compression shirt, socks) includes an anti-anxiety active (e.g., cannabidiol). Based on biometric data (e.g., heart rate data from a heart rate sensor, EDA data from an EDA sensor, movement data from a movement sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the anti-anxiety active. Advantageously, this helps decrease symptoms of anxiety in a wearer. The at least one delivery device is also operable to decrease the voltage to the one or more of the at least one conductive and/or electromagnetic yarn, yarn precursor, thread, filament, and/or fiber based on the biometric data.

In yet another example, at least one delivery device (e.g., tights, leggings) includes a restless leg syndrome treatment (e.g., rotigotine, magnesium). Based on biometric data (e.g., movement data from a movement sensor, EMG data from an EMG sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the restless leg syndrome treatment. Advantageously, this helps decrease symptoms of restless leg syndrome in a wearer. The at least one delivery device is also operable to decrease the voltage to the one or more of the at least one conductive and/or electromagnetic yarn, yarn precursor, thread, filament, and/or fiber based on the biometric data.

In still another example, at least one delivery device (e.g., joint brace) includes a pain reliever (e.g., aspirin, local anesthetic, capsaicin, capsaicinoid). Based on biometric data (e.g., heart rate data from a heart rate sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the pain reliever. Advantageously, this helps decrease pain in a wearer. The at least one delivery device is also operable to decrease the voltage to the one or more of the at least one conductive and/or electromagnetic yarn, yarn precursor, thread, filament, and/or fiber based on the biometric data.

In one example, at least one delivery device (e.g., shirt, leggings, socks) includes a blood pressure medication (e.g., clonidine). Based on biometric data (e.g., blood pressure data from a blood pressure sensor, heart rate data from a heart rate sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the blood pressure medication. Advantageously, this helps decrease blood pressure in a wearer. The at least one delivery device is also operable to decrease the voltage to the one or more of the at least one conductive and/or electromagnetic yarn, yarn precursor, thread, filament, and/or fiber based on the biometric data.

In another example, at least one delivery device (e.g., shirt, leggings, socks, wrist band) includes a motion sickness medication (e.g., scopolamine). Based on biometric data (e.g., movement sensor data from a movement sensor) and/or environmental data (e.g., motion sensor data from motion sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the motion sickness medication. Advantageously, this helps address motion sickness severity based on motion. The at least one delivery device is also operable to decrease the voltage to the one or more of the at least one conductive and/or electromagnetic yarn, yarn precursor, thread, filament, and/or fiber based on the biometric data and/or the environmental data.

In yet another example, at least one delivery device (e.g., shirt, leggings) includes an odor mitigant (e.g., perfume). Based on biometric data (e.g., odor sensor data from odor sensor) and/or environmental data (e.g., air quality sensor data from air quality sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the odor mitigant. Advantageously, this helps address odor over time. The at least one delivery device is also operable to decrease the voltage to the one or more of the at least one conductive and/or electromagnetic yarn, yarn precursor, thread, filament, and/or fiber based on the biometric data and/or the environmental data.

In still another example, at least one delivery device (e.g., shirt, leggings, gloves socks) includes a skin moisturizer (e.g., cocoa butter). Based on biometric data (e.g., EDA sensor data from EDA sensor) and/or environmental data (e.g., humidity sensor data from humidity sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the skin moisturizer. Advantageously, this helps address skin dryness based on skin conductivity and/or environmental humidity. The at least one delivery device is also operable to decrease the voltage to the one or more of the at least one conductive and/or electromagnetic yarn, yarn precursor, thread, filament, and/or fiber based on the biometric data and/or the environmental data.

In another example, at least one delivery device (e.g., gloves, socks, wrist band) includes a smoking cessation aid (e.g., nicotine). Based on biometric data (e.g., heart rate data from a heart rate sensor, movement data from a movement sensor), the heater applies a voltage to one or more of the at least one conductive and/or electromagnetic yarn, yarn precursor, thread, filament, and/or fiber. The applied voltage increases a temperature of the one or more of the at least one conductive and/or electromagnetic yarn, yarn precursor, thread, filament, and/or fiber, which increases the rate of release of the smoking cessation aid. Advantageously, this helps reduce nicotine dependence. In one embodiment, the at least one delivery device is operable to increase and/or decrease a rate of release based on the clock (e.g., timed delivery intervals). The at least one delivery device is also operable to decrease the voltage to the one or more of the at least one conductive and/or electromagnetic yarn, yarn precursor, thread, filament, and/or fiber based on the biometric data and/or the clock.

In a preferred embodiment, the least one remote device is operable to adjust parameters of the delivery device. In one embodiment, the at least one remote device includes a user interface (e.g., graphical user interface (GUI)) that allows the delivery system to adjust parameters (e.g., temperature of the heater) of the delivery device (e.g., based on user input). For example, and not limitation, in one embodiment, a release rate of the delivery system is adjusted based on input from the at least one remote device. In one embodiment, the at least one remote device includes a mobile application (e.g., for a smartphone or tablet).

In one embodiment, the delivery device is selectively activated and/or selectively deactivated based on a trigger event. In one embodiment, the parameters of the delivery device are adjusted based on a trigger event. In one embodiment, the trigger event is a threshold. In one embodiment, the threshold is related to the biometric data, the environmental data, and/or the clock. The parameters include, but are not limited to, turning on a voltage, turning off the voltage, decreasing the voltage, and/or increasing the voltage. Alternatively, the parameters of the delivery device are adjusted based on input from the at least one remote device (e.g., user input). In one embodiment, the delivery device is activated and/or deactivated based on input from the at least one remote device (e.g., user input). In another embodiment, the delivery device is activated and/or deactivated using a power button or switch on the delivery device.

In one embodiment, the system further includes a feedback loop. In one embodiment, parameters of the delivery device are adjusted based on the biometric data, the environmental data, and/or the clock in the feedback loop. In one embodiment, the system receives the biometric data and/or the environmental data in real time and/or near-real time. In one embodiment, the delivery device is operable to adjust parameters of the delivery device in real time and/or near-real time. In another embodiment, the system receives the biometric data and/or the environmental data in predefined intervals (e.g., 5 minutes, 10 minutes, 15 minutes, 30 minutes, etc.). In one embodiment, the delivery device is operable to adjust parameters of the delivery device in predetermined intervals. In one embodiment, the predefined intervals are equivalent to the predetermined intervals. Alternatively, the predefined intervals are not equivalent to the predetermined intervals.

The mobile application preferably includes activity data including, but not limited to, at least one activity (e.g., physical exercise, sleep, work), a start time of the at least one activity, an end time of the at least one activity, a duration of the at least one activity, and/or a distance related to the at least one activity. The mobile application is further operable to receive biometric data from the at least one body sensor. In a preferred embodiment, the mobile application is operable to receive biometric data and/or health information from at least one third party application (e.g., APPLE HEALTH).

The mobile application is operable to synchronize to at least one delivery device. During synchronization, the mobile application receives the unique device ID number and/or the data related to the at least one active compound. For example, and not limitation, the mobile application synchronizes with a first delivery device having a first device ID number and at least one first active compound (e.g., a muscle recovery or muscle stimulation aid) and a second delivery device having a second device ID number and at least one second active compound (e.g., sleep aid). The mobile application is operable to receive first activity data (e.g., physical exercise data) related to use of the first delivery device and second activity data (e.g., sleep data) related to use of the second delivery device (e.g., via the user interface).

In one embodiment, the mobile application includes at least one baseline biometric data. For example, and not limitation, the mobile application includes an average heart rate, an average body temperature, and/or an average resting heart rate. In one embodiment, when at least one biometric data exceeds a threshold related to the at least one baseline biometric data and/or returns to within the threshold, the mobile application is operable to adjust parameters of the delivery device. In one example, an average heart rate of a wearer is 70. When heart rate data is exceeds a threshold (e.g., more than 20 over average (>90.01)), an applied voltage increases a temperature of the one or more of the at least one conductive and/or electromagnetic yarn, yarn precursor, thread, filament, and/or fiber, which increases the rate of release of an anti-anxiety active. When heart rate data returns to within the threshold (e.g., less than or equal to 20 over average (≤90)), the applied voltage decreases the temperature of the one or more of the at least one conductive and/or electromagnetic yarn, yarn precursor, thread, filament, and/or fiber, which decreases the rate of release of the anti-anxiety active.

In one embodiment, the mobile application is operable to access a camera on the remote device. The mobile application is preferably operable to perform image analysis on at least one image (e.g., still, video) taken by the camera. In one embodiment, the mobile application is operable to assess at least one skin condition. See, e.g., WIPO Publication No. 2021086594, which is incorporated herein by reference in its entirety. In one embodiment, the mobile application is further operable to make at least one recommendation for at least one delivery device (e.g., duration of use, type of delivery device, active compound, etc.) based on the image analysis.

The delivery system is operable to utilize a plurality of learning techniques including, but not limited to, machine learning (ML), artificial intelligence (AI), deep learning (DL), neural networks (NNs), artificial neural networks (ANNs), support vector machines (SVMs), Markov decision process (MDP), and/or natural language processing (NLP). The delivery system is operable to use any of the aforementioned learning techniques alone or in combination.

Further, the delivery system is operable to utilize predictive analytics techniques including, but not limited to, machine learning (ML), artificial intelligence (AI), neural networks (NNs) (e.g., long short term memory (LSTM) neural networks), deep learning, historical data, and/or data mining to make future predictions and/or models. The delivery system is preferably operable to recommend and/or perform actions based on historical data, external data sources, ML, AI, NNs, and/or other learning techniques. The delivery system is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

Location data is created in the present invention using one or more hardware and/or software components. By way of example and not limitation, location data is created using the Global Positioning System (GPS), low energy BLUETOOTH based systems such as beacons, wireless networks such as WIFI, Radio Frequency (RF) including RF Identification (RFID), Near Field Communication (NFC), magnetic positioning, and/or cellular triangulation. By way of example, location data is determined via an Internet Protocol (IP) address of a device connected to a wireless network. A wireless router is also operable to determine identities of devices connected to the wireless network through the router, and thus is operable to determine the locations of these devices through their presence in the connection range of the wireless router.

Figure 5:
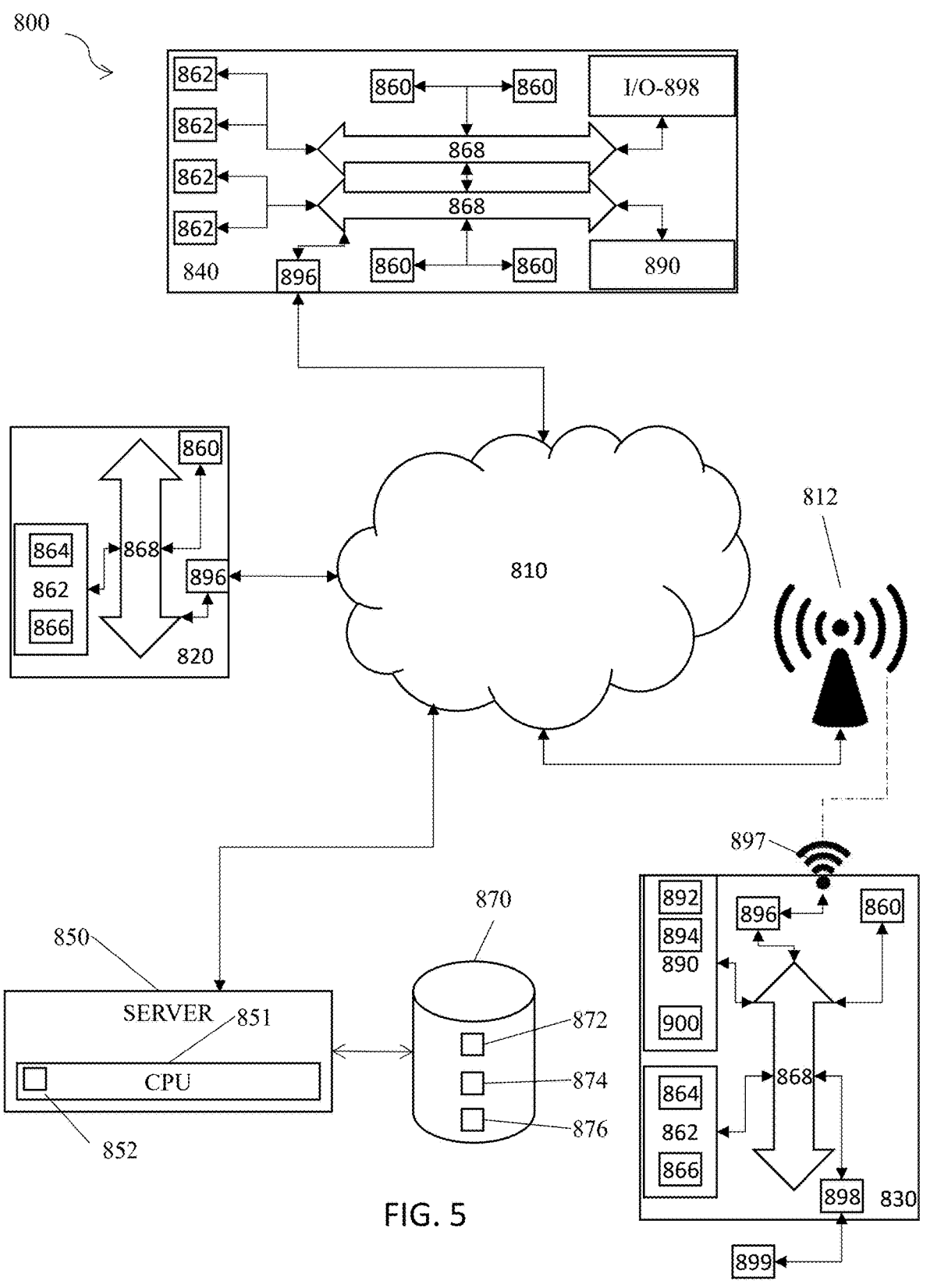
FIG. 5 is a schematic diagram of a system of the present invention.

FIG. 5 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICROWAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, signal generation devices (e.g., speakers), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 5, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 5, is operable to include other components that are not explicitly shown in FIG. 5, or is operable to utilize an architecture completely different than that shown in FIG. 5. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:

1. An article for delivery of an active compound to the skin of a user comprising:
a textile including at least one printed circuit board (PCB), wherein the at least one PCB includes a processor, a heater, a memory, and a battery;
wherein the textile comprises at least one electromagnetic fiber and at least one loaded fiber, wherein the loaded fiber comprises a polymeric matrix including at least one active compound;
wherein a heater is disposed on or integrated with the at least one PCB and is operable to generate a voltage,
wherein the voltage is electrically transmitted from the at least one PCB to the at least one electromagnetic fiber;
wherein the voltage is conducted by the at least one electromagnetic fiber;
wherein increasing the voltage increases the temperature of the loaded fiber, wherein increasing the temperature of the loaded fiber increases the rate of release of the at least one active compound; and
wherein decreasing the voltage decreases the temperature of the loaded fiber, wherein decreasing the temperature of the loaded fiber decreases the rate of release of the at least one active compound.

2. The article of claim 1, wherein the textile further comprises at least one sensor, wherein the at least one sensor detects physiological data relating to the physiological condition of a user and/or environmental data relating to the environment of the user.

3. The article of claim 2, wherein the at least one PCB is operable to analyze the physiological data and/or the environmental data detected by the at least one sensor and increase and/or decrease the voltage based on analysis of the data.

4. The article of claim 1, further comprising;
a user device and a remote server including a database;
wherein the user device is in network communication with the at least one PCB and the remote server;
wherein the database is operable to store at least one user profile associated with the user device; and
wherein the user device receives an input via a graphic user interface (GUI) and analyzes the input using an analytics engine, wherein the user device is operable to transmit a signal to the at least one PCB to increase and/or decrease the voltage based on the analysis of the input.

5. The article of claim 4, wherein the user device is operable to receive activity data and store the activity data on the database of the remote server, wherein the activity data includes at least one activity, a start time of the at least one activity, and an end time of the at least one activity.

6. The article of claim 1, wherein the at least one PCB is operable to increase and/or decrease the voltage in time-based intervals.

7. The article of claim 1, wherein the at least one electromagnetic fiber is a fiber coated with at least one layer of electrically conductive ink and/or formed from at least one electromagnetic material selected from a group consisting of stainless steel, copper, aluminum, gold, silver, tungsten, iron, titanium, chromium, platinum, palladium, and nickel.

8. The article of claim 1, wherein the textile is incorporated into a wearable garment, bedding, toweling, an orthopedic cast, a wound dressing, a bandage, a skin guard, a wrist band, an arm band, a knee pad, an athletic supporter, a robe, a neck band, a head band, a pair of gloves, a diaper, or a joint brace.

9. A system for automatic delivery of an active compound to the skin of a user comprising:
a textile, at least one user device, and at least one server including at least one database;
wherein the at least one server is in network communication with the at least one user device;
wherein the at least one user device includes a graphical user interface (GUI) and an analytics engine;
wherein the at least one database stores at least one user profile and at least one set of parameters for data correlating to the at least one user profile associated with the at least one user device;
wherein the textile comprises a printed circuit board (PCB) and at least one sensor, wherein the at least one sensor collects physiological data and/or environmental data relating to a physiological condition and/or an environmental condition associated with the at least one user profile;
wherein the at least one sensor is operable to transmit the physiological data and/or the environmental data to the at least one user device;

wherein the analytics engine is operable to analyze the transmitted physiological data and/or the transmitted environmental data in view of the at least one user profile to determine that the physiological data and/or the environmental data does not meet the at least one set of parameters;
wherein the textile further comprises at least one electromagnetic fiber and at least one loaded fiber, wherein the at least one loaded fiber comprises a polymeric matrix including an active compound;
wherein a processor of the at least one PCB receives a signal from the at least one user device, wherein a heater generates a voltage in response to the received signal, wherein the voltage is electrically transmitted from the at least one PCB to the at least one electromagnetic fiber, wherein the voltage is conducted by the at least one electromagnetic fiber;
wherein increasing the voltage increases the temperature of the loaded fiber, wherein increasing the temperature of the loaded fiber increases the rate of release of the at least one active compound; and
wherein decreasing the voltage decreases the temperature of the loaded fiber, wherein decreasing the temperature of the loaded fiber decreases the rate of release of the at least one active compound.

10. The system of claim 9, wherein upon determination that the physiological data and/or the environmental data collected by the sensor does not fall within at least one input parameter, the at least one PCB is operable to increase and/or decrease the voltage.

11. The system of claim 9, wherein the at least one PCB is operable to determine a baseline for the physiological data and/or the environmental data, wherein upon determination that the physiological data and/or the environmental data exceeds an objective parameter related to the baseline the PCB is operable to increase and/or decrease the voltage.

12. The system of claim 9, wherein the at least one PCB of at least two textiles are operable to be connected to a single user device.

13. The system of claim 9, wherein the at least one user device is operable to connect to a global positioning system (GPS), wherein the at least one PCB is operable to increase the voltage based on a location of the at least one user device.

14. The system of claim 9, wherein the at least one database is operable to store medical information associated with the at least one user profile.

15. The system of claim 9, wherein the user device is operable to receive activity data and store the activity data on the database of the remote server, wherein the activity data includes at least one activity, a start time of the at least one activity, and an end time of the at least one activity.

16. The system of claim 9, wherein the textile is incorporated into a wearable garment, bedding, toweling, an orthopedic cast, a wound dressing, a bandage, a skin guard, a wrist band, an arm band, a knee pad, an athletic supporter, a robe, a neck band, a head band, a pair of gloves, a diaper, or a joint brace.

17. A system for automatic delivery of an active compound to the skin of a user comprising:
a textile including at least one printed circuit board (PCB) and a heater, wherein the at least one PCB comprises a processor, a memory, and a battery, wherein the heater is disposed on or integrated with the at least one PCB; and
at least one user device and at least one server including at least one database;

US 12,629,342 B1

39 wherein the at least one server is in network communication with the at least one user device;

wherein the at least one server stores at least one user profile associated with the at least one user device, wherein the at least one user profile comprises medical history, biometric history, environmental data history, and system preferences;

wherein the at least one user device includes a graphical user interface (GUI) configured to receive and display biometric data, and to allow adjustment of delivery parameters by a user;

wherein the at least one user device is in network communication with the at least one PCB;

wherein the textile comprises at least one electromagnetic fiber and at least one loaded fiber, wherein the at least one loaded fiber comprises an active compound dispersed within a polymeric matrix;

wherein the at least one PCB receives a signal from the at least one user device to trigger the release of the active compound from the at least one loaded fiber; and

40 wherein the at least one PCB transmits the signal to the heater, wherein the heater applies a voltage to the at least one electromagnetic fiber.

18. The system of claim 17, wherein the at least one user device is operable to connect to a global positioning system (GPS), wherein the at least one PCB is operable to increase the voltage based on a location of the at least one user device.

19. The system of claim 17, wherein the at least one user device receives an input via a graphic user interface (GUI) and analyzes the input using an analytics engine, wherein the user device is operable to transmit a signal to the at least one PCB to increase and/or decrease the applied voltage based on an analysis of the input from the analytics engine.

20. The system of claim 17, wherein the at least one PCB of at least two textiles are operable to connect to a single user device.

* * * * *